United States Patent
Prockop et al.

(10) Patent No.: US 10,351,825 B2
(45) Date of Patent: Jul. 16, 2019

(54) MESENCHYMAL STEM CELLS DERIVED FROM INDUCED PLURIPOTENT STEM CELLS

(71) Applicants: THE TEXAS A&M UNIVERSITY SYSTEM, College Station, TX (US); TEMPLE THERAPEUTICS, INC., Framingham, MA (US); Darwin J. Prockop, Philadelphia, PA (US); Fei Liu, Belton, TX (US); Qingguo Zhao, Temple, TX (US); Barry A. Berkowitz, Framingham, MA (US)

(72) Inventors: Darwin J. Prockop, Philadelphia, PA (US); Fei Liu, Belton, TX (US); Qingguo Zhao, Temple, TX (US); Barry A. Berkowitz, Framingham, MA (US)

(73) Assignees: The Texas A&M University System, College Station, TX (US); Temple Therapeutics, Inc., Framingham, MA (US)

(*) Notice: Subject to any disclaimer, the term of this patent is extended or adjusted under 35 U.S.C. 154(b) by 0 days.

(21) Appl. No.: 15/323,893

(22) PCT Filed: Jul. 8, 2015

(86) PCT No.: PCT/US2015/039532
§ 371 (c)(1),
(2) Date: Jan. 4, 2017

(87) PCT Pub. No.: WO2016/081032
PCT Pub. Date: May 26, 2016

(65) Prior Publication Data
US 2017/0145385 A1 May 25, 2017

Related U.S. Application Data

(60) Provisional application No. 62/023,480, filed on Jul. 11, 2014.

(51) Int. Cl.
*A61K 35/28* (2015.01)
*C12N 5/0775* (2010.01)

(52) U.S. Cl.
CPC ............ *C12N 5/0668* (2013.01); *A61K 35/28* (2013.01); *C12N 2501/15* (2013.01); *C12N 2501/602* (2013.01); *C12N 2501/603* (2013.01); *C12N 2501/604* (2013.01); *C12N 2501/606* (2013.01); *C12N 2506/45* (2013.01)

(58) Field of Classification Search
None
See application file for complete search history.

(56) References Cited

U.S. PATENT DOCUMENTS

| | | | | |
|---|---|---|---|---|
| 2010/0278790 A1* | 11/2010 | Prockop | ............... | C07K 14/525 424/93.21 |
| 2012/0009618 A1 | 1/2012 | Yu et al. | | |
| 2013/0280222 A1* | 10/2013 | Kay | ....................... | C12N 15/85 424/93.21 |
| 2014/0099717 A1 | 4/2014 | Fraker et al. | | |

OTHER PUBLICATIONS

Malik et al., Pluripotent Stem Cells pp. 23-33 Part of the Methods in Molecular Biology book series (MIMB, vol. 997) A Review of the Methods for Human iPSC Derivation.*
Diederichs et al. Functional Comparison of Human-Induced Pluripotent Stem Cell-Derived Mesenchymal Cells and Bone Marrow-Derived Mesenchymal Stromal Cells from the Same Donor Stem Cells and Development vol. 23, No. 14, 2014 pp. 1594-1610.*
Prabakar et al Generation of Glucose-Responsive, Insulin-Producing Cells From Human Umbilical Cord Blood-Derived Mesenchymal Stem CellsCell Transplantation, vol. 21, No. 6, 2012, pp. 1321-1339(19).*
Dominici et al.Position Paper Minimal criteria for defining multipotent mesenchymal stromal cells. The International Society for Cellular Therapy position statement (Cytotherapy (2006) vol. 8, No. 4, 315-317).*
Viswanathan et al., Soliciting Strategies for Developing Cell-Based Reference Materials to Advance Mesenchymal Stromal Cell Research and Clinical TranslationStem Cells and Development vol. 23, No. 11,2014; pp. 1157-1167.*
Trivedi et al Derivation and immunological characterization of mesenchymal stromal cells from human embryonic stem cellsDerivation and immunological characterization of mesenchymal stromal cells from human embryonic stem cells Experimental Hematology 36 (2008) 350-359.*

* cited by examiner

*Primary Examiner* — Maria G Leavitt
(74) *Attorney, Agent, or Firm* — Raymond J. Lillie

(57) ABSTRACT

A method of producing mesenchymal stem cells from induced pluripotent stem cells in which induced pluripotent stem cells are cultured in the presence of a TGF-β inhibitor an in an atmosphere containing from about 7 vol. % to about 8 vol. % $CO_2$ for a period of time from about 20 day to about 35 days. The cells then are transferred to a culture dish having a hydrophilic surface, and the cells are cultured in a medium containing a TGF-β inhibitor for a period of time sufficient to produce mesenchymal stem cells. Such mesenchymal stem cells are more stable and less likely to form tumors, cancers, or teratomas. Also, the induced pluripotent stem cells may be genetically engineered with at least one polynucleotide encoding a therapeutic agent and then are cultured as hereinabove described to provide genetically engineered mesenchymal stem cells that express sustained amounts of a biologically active protein or polypeptide.

12 Claims, 17 Drawing Sheets
Specification includes a Sequence Listing.

OSTEOGENESIS

CHONDROGENESIS

ADIPOGENESIS

```
                        SEQUENCE LISTING

<160> NUMBER OF SEQ ID NOS: 1

<210> SEQ ID NO 1
<211> LENGTH: 277
<212> TYPE: PRT
<213> ORGANISM: Homo sapiens
<220> FEATURE:
<223> OTHER INFORMATION: TSG-6 protein

<400> SEQUENCE: 1

Met Ile Ile Leu Ile Tyr Leu Phe Leu Leu
1               5                   10

Leu Trp Glu Asp Thr Gln Gly Trp Gly Phe
                15                  20

Lys Asp Gly Ile Phe His Asn Ser Ile Trp
                25                  30

Leu Glu Arg Ala Ala Gly Val Tyr His Arg
                35                  40

Glu Ala Arg Ser Gly Lys Tyr Lys Leu Thr
                45                  50

Tyr Ala Glu Ala Lys Ala Val Cys Glu Phe
                55                  60

Glu Gly Gly His Leu Ala Thr Tyr Lys Glu
                65                  70

Leu Glu Ala Ala Arg Lys Ile Gly Phe His
                75                  80

Val Cys Ala Ala Gly Trp Met Ala Lys Gly
                85                  90

Arg Val Gly Tyr Pro Ile Val Lys Pro Gly
                95                  100

Pro Asn Cys Gly Phe Gly Lys Thr Gly Ile
                105                 110

Ile Asp Tyr Gly Ile Arg Leu Asn Arg Ser
                115                 120

Glu Arg Trp Asp Ala Tyr Cys Tyr Asn Pro
                125                 130

His Ala Lys Glu Cys Gly Gly Val Phe Thr
```

-continued

```
            135                 140
Asp Pro Lys Glu Ile Phe Lys Ser Pro Gly
            145                 150

Phe Pro Asn Glu Tyr Glu Asp Asn Gln Ile
            155                 160

Cys Tyr Trp His Ile Arg Leu Lys Tyr Gly
            165                 170

Gln Arg Ile His Leu Ser Phe Leu Asp Phe
            175                 180

Asp Leu Glu Asp Asp Pro Gly Cys Leu Ala
            185                 190

Asp Tyr Val Glu Ile Tyr Asp Ser Tyr Asp
            195                 200

Asp Val His Gly Phe Val Gly Arg Tyr Cys
            205                 210

Gly Asp Glu Leu Pro Asp Asp Ile Ile Ser
            215                 220

Thr Gly Asn Val Met Thr Leu Lys Phe Leu
            225                 230

Ser Asp Ala Ser Val Thr Ala Gly Gly Phe
            235                 240

Gln Ile Lys Tyr Val Ala Met Asp Pro Val
            245                 250

Ser Lys Ser Ser Gln Gly Lys Asn Thr Ser
            255                 260

Thr Thr Ser Thr Gly Asn Lys Asn Phe Leu
            265                 270

Ala Gly Arg Phe Ser His Leu
            275
```

MESENCHYMAL STEM CELLS DERIVED FROM INDUCED PLURIPOTENT STEM CELLS

This application claims priority based on provisional Application Ser. No. 62/023,480, filed Jul. 11, 2014, the contents of which are incorporated by reference in their entirety.

This invention relates to mesenchymal stem cells, or MSCs, including human mesenchymal stem cells. More particularly, this invention relates to mesenchymal stem cells produced from induced pluripotent stem cells (iPSCs), wherein the iPSCs are cultured under conditions to provide mesenchymal stem cells that are less likely to produce tumors or cancers and are more stable. Prior to being cultured under conditions to produce mesenchymal stem cells, the iPSCs may be genetically engineered with at least one polynucleotide encoding at least one biologically active protein or polypeptide or biologically active fragment, derivative, or analogue thereof, thus enabling one to produce genetically engineered mesenchymal stem cells from the genetically engineered iPSCs that express sustained levels of the at least one biologically active protein or polypeptide, or biologically active fragment, derivative, or analogue thereof.

The use of mesenchymal stromal or stem cells (MSCs) in cancer patients or cancer survivors is a promising strategy to improve treatment of advanced cancer (Droujinine et al., 2013), and to repair tissue damage by cancers or by radical cancer therapies (Zimmerlin et al., 2013). Based on the unique homing capability of tissue-derived MSCs to stroma of various primary and metastatic cancers (Chaturvedi et al., 2013; Jung et al., 2013; Quante et al., 2011; Song and Li, 2011), MSCs have the potential to treat or even eliminate various cancers by delivering various anti-cancer agents (Lee et al., 2012; Loebinger et al., 2009) (Grisendi et al., 2010). Because of their potential for differentiation (Pittenger et al., 1999; Prockop, 1997) and production of immunomodulatory, angiogenic, anti-apoptotic, anti-scarring, and pro-survival factors (Meirelles Lda et al., 2009), MSCs have shown promising regeneration potential after radical cancer treatment in animal models, such as soft tissue reconstruction after disfiguring surgeries for head, neck or breast cancers (Donnenberg et al., 2010), and salivary gland regeneration for head and neck cancer patients treated with radiotherapy (Lin et al., 2011; Sumita et al., 2011). As one example, the combination of osteogenic potential and targeted delivery of anticancer agents make MSCs a promising option to treat tumor-induced osteolysis (Fritz et al., 2008; Li et al., 2011). Exogenous tissue-derived MSCs, however, including those from bone marrow, adipose tissues, or umbilical cord, all have shown a tendency to promote rather than inhibit cancers in many circumstances (Barkholt et al., 2013; Karnoub et al., 2007; Li et al., 2012; Liu et al., 2011) (Gu et al., 2012; Klopp et al., 2012). Also, endogenous MSCs are a major source of reactive stromal cells that promote growth and metastasis of cancers (Kidd et al., 2012; Quante et al., 2011).

Moreover, MSCs have a limited proliferation potential and lose some of their important biological functions as they are expanded (Larson et al., 2010). Therefore, it is difficult to prepare large banks of the cells with uniform biological activities and/or transgene expression required for experiments in large animals and for future clinical therapies. Another problem is that MSCs are being prepared with a variety of protocols in different laboratories from different donors. As a result, standardization of the cells has been extremely difficult and the data presented in different publications is difficult to compare. Therefore, large banks of reference cells are needed to advance the MSC research (Viswanathan et al., 2014).

In order to address the limitations of expandability and standardization, MSCs were derived from induced pluripotent stem cells (iPSCs) with a modified protocol that can be expanded to provide large cell banks from a single cell clone. The protocol produces highly enriched MSC-like cells from iPSCs with high efficiency. The iPSC-derived MSCs (iPSC-MSCs) express the classical surface markers of MSCs, are capable of multi-lineage mesodermal differentiation and cancer homing, can be expanded extensively, but do not preserve the pluoripotency of iPSCs. Surprisingly, iPSC-MSCs do not promote epithelial-mesenchymal transition (EMT), invasion and stemness of cancer cells as is seen with bone marrow-derived MSCs (BM-MSCs). Consistent with these observations, the iPSC-MSCs express much lower levels than BM-MSCs of pro-tumor factors including interleukin-6, prostaglandin E2, SDF1, and hyaluronan before and after exposure to tumor micro-environment. The data indicated that iPSC-MSCs are a safe alternative to BM-MSCs for cancer therapy and other applications with better expandability and potential for genetic engineering.

In accordance with an aspect of the present invention, there is provided a method of producing mesenchymal stem cells from induced pluripotent stem cells. The method comprises culturing the induced pluripotent stem cells in a medium containing a TGF-β inhibitor (also known as an Smad 2/3 pathway) inhibitor and in an atmosphere containing from about 7 vol % to about 8 vol. % carbon dioxide ($CO_2$) for a period of time of from about 20 days to about 35 days. The cells then are transferred to a culture dish having a hydrophilic surface, and the cells are cultured in a medium containing a TGF-β inhibitor for a period of time sufficient to produce mesenchymal stem cells. The mesenchymal stems cells then may be isolated from the culture medium by means known to those skilled in the art.

In a non-limiting embodiment, the mesenchymal stem cells are mammalian mesenchymal stem cells produced from mammalian induced pluripotent stem cells. In another non-limiting embodiment, the mammal is a primate. In yet another non-limiting embodiment, the primate is a human.

The TGF-β inhibitor may, in a non-limiting embodiment, be selected from those known to those skilled in the art. In a non-limiting embodiment, the TGF-β inhibitor is a product known as SB-431542 (Sanchez, et al., 2011), sold by Sigma-Aldrich, St. Louis, Mo.

In another non-limiting embodiment, the induced pluripotent stem cells are cultured in an atmosphere containing about 7.5 vol. % $CO_2$.

In another non-limiting embodiment, the induced pluripotent stem cells are cultured in the medium containing the TFG-β inhibitor and in the atmosphere containing from about 7wt. % to about 8 wt. % $CO_2$ for a period of time of about 25 days.

In another non-limiting embodiment, after the cells are cultured in the medium containing the TGF-β inhibitor and in an atmosphere containing from about 7 vol. % to about 8 vol. % $CO_2$ for from about 20 days to about 35 days, the cells are transferred to a culture dish having an oxygenated surface, which makes the surface hydrophilic. Such culture dishes in general may be standard tissue culture plastic dishes known to those skilled in the art. In such culture dishes, there is a culture medium containing a TGF-β inhibitor, such as SB-43152, for example. In another non-limiting embodiment, the cells are cultured in such culture dish and in the medium containing a TGF-β inhibitor for a period of time of about 21 days, thereby providing a culture of mesenchymal stem cells derived from induced pluripotent stem cells.

In a non-limiting embodiment, induced pluripotent stem cells are cultured in a medium, such as the feeder-free medium mTeSR1 (STEMCELL Technologies) that has been supplemented with a TGF-β inhibitor such as SB431542 in an atmosphere containing 7.5 vol. % $CO_2$ for 25 days. The cells then are transferred to a tissue culture plastic dish having a hydrophilic surface, and which contains a medium, such as a modified human ES-MSC medium containing knockout serum replacement, nonessential amino acids, antibiotic such as penicillin and streptomycin, glutamine, β-mercaptoethanol, and bFGF, which has been supplemented with a TGF-β inhibitor such as SB-431542. The medium is changed daily, and the cells are passaged at 80%-90% confluence about every 3 days. The cells are cultured for a total of about 21 days to provide a majority of cells that are positive for MSC surface markers. Such mesenchymal stem cells also are known as iPSC-MSCs. The iPSC-MSCs then can be cultured in the presence of a standard medium, such as 20% fetal bovine serum (FBS) α-MEM medium, and then harvested for further experiments or for use in treating diseases or disorders, or for regenerating cells, tissues, or organs.

The mesenchymal stem cells formed from the induced pluripotent stem cells in accordance with the present invention thus have several desirable properties and characteristics that make the mesenchymal stem cells more stable, and whereby such mesenchymal stem cells are less likely to form or cause tumors, cancers, or teratomas, and thus are more desirable for use in therapy than other mesenchymal stem cells.

Thus, in accordance with another aspect of the present invention, there are provided isolated human mesenchymal stem cells derived from human induced pluripotent stem cells that express no more than 1% of the levels of the Nanog, Oct. 4, Ecad, and Foxa2 genes than the induced pluripotent stem cells from which the mesenchymal stem cells were derived.

In a non-limiting embodiment, the isolated human mesenchymal stem cells are at least 95% positive for the epitopes CD73, CD105, and CD166. In another non-limiting embodiment, the isolated human mesenchymal stem cells are at least 85% positive for the epitopes CD44 and CD90.

In yet another non-limiting embodiment, the isolated human mesenchymal stem cells are no more than 5% positive for the epitopes HLA-DR, CD11b, CD24, CD34, and CD45.

Furthermore, the isolated human mesenchymal stem cells of the present invention, in a non-limiting embodiment, contain the following levels of messenger RNAs (mRNAs) relative to a standardized preparation of MSC obtained from bone marrow (Sample No. 7075, available from the Institute for Regenerative Medicine, Texas A&M College of Medicine, Temple, Texas 76502): about 80% to about 120% of the mesodermal marker CD140A, about 550% to about 650% of the angiogenic gene VEGF, and less than 20%±5% of the following genes known to promote the growth and metastasis of cancer cells: ILR1, mPGES1, IL-6, TGF-βR2, ID3, SDF1, HAS1, and HAS2.

The isolated human mesenchymal stem cells of the present invention also stop dividing in culture after 70 to 100 population doublings under conditions in which MSCs obtained from bone marrow also stop dividing and therefore are less likely than immortal cells to produce tumors or cancers in patients, and are less likely to form teratomas in culture or tumors after injection into immunodeficient animals, such as immunodeficient mice.

The isolated human mesenchymal stem cells of the present invention may be administered in an amount effective to treat a variety of diseases and disorders, and to regenerate a variety of cells, tissues, and organs. The isolated human mesenchymal stem cells may be administered systematically such as by intramuscular, intravenous, intraperitoneal or intra-arterial administration or may be administered directly to an affected cell, tissue, or organ. The isolated human mesenchymal stem cells may be administered in conjunction with an acceptable pharmaceutical carrier adjuvant or excipient known to those skilled in the art. Such diseases and disorders include, but are not limited to, inflammatory diseases, disorders, and conditions, eye diseases and disorders, such as macular degeneration, diseases of the cornea, eye injuries, including corneal injuries, cardiac disease, including myocardial infarction, brain injury, brain trauma, brain diseases and disorders, including stroke and Alzheimer's disease, neuro motor diseases such as Parkinson's Disease, autoimmune diseases, including diabetes, obesity, and tumors, including malignant and non-malignant tumors.

Cells, tissues, or organs which may be regenerated in accordance with the isolated human mesenchymal stem cells of the present invention include, but are not limited to, bone tissue, eye tissue, including corneal tissue, cardiac tissue, including cardiac muscle and the coronary arteries, as well as any other cell, tissue or organ known to be regenerated by mesenchymal stem cells.

The exact dosage of mesenchymal stem cells to be administered is dependent upon a variety of factors, including but not limited to the age, weight, height, and sex of the patient, the disease or disorder being treated, and the extent and severity thereof, or the cells, tissue, or organ to be regenerated.

It is to be understood, however, that the scope of the present invention is not intended to be limited to the treatment of any particular disease, condition, or disorder, or to the regeneration of any particular cell, tissue, or organ.

The isolated human mesenchymal stem cells of the present invention, prepared as hereinabove described, and having the properties hereinabove described, may be genetically engineered with at least one polynucleotide encoding at least one biologically active protein or polypeptide or biologically active fragment, derivative, or analogue thereof. Thus, in accordance with an aspect of the present invention, there is provided a method of producing genetically engineered mesenchymal stem cells from induced pluripotent stem cells. The method comprises introducing into the induced pluripotent stem cells at least one polynucleotide encoding at least one biologically active protein or polypeptide, or biologically active fragment, analogue, or derivative thereof to provide genetically engineered induced pluripotent stem cells. The genetically engineered pluripotent stem cells then are cultured as hereinabove described to produce genetically engineered mesenchymal stem cells, such as mammalian mesenchymal stem cells. In a non-limiting embodiment, the genetically engineered mammalian mesenchymal stem cells are primate mesenchymal stem cells, including human mesenchymal stem cells.

Thus, the genetically engineered induced pluripotent stem cells are cultured in a medium containing a TGF-β inhibitor and in an atmosphere containing from about 7 vol. % to about 8 vol. % $CO_2$ (about 7.5 vol. % $CO_2$ in another non-limiting embodiment) for a period of time of from about 20 days to about 35 days (about 25 days in another non-limiting embodiment). The genetically engineered cells then are transferred to a culture dish having a hydrophilic surface, such as those hereinabove described, and cultured in a medium containing a TGF-β inhibitor for a period of time (in a non-limiting embodiment, 21 days) sufficient to produce genetically engineered mesenchymal stem cells.

The at least one polynucleotide including at least one biologically active protein or polypeptide or biologically active fragment or derivative may be in the form of DNA (including but not limited to genomic DNA (gDNA) or cDNA, or RNA. The at least one polynucleotide encoding at least one biologically active protein or polypeptide or biologically active fragment, derivative, or analogue thereof may be contained in an appropriate expression vector, such as an adenoviral vector, adeno-associated virus vector, retroviral vector, or lentiviral vector that is introduced into the induced pluripotent stem cells, or may be contained in a transposon that is introduced into the cell, or the at least one polynucleotide may be introduced into the cell as naked DNA or RNA. Such introduction of the at least one polynucleotide may be introduced into the cell by any of a variety of means known to those skilled in the art, such as calcium phosphate precipitation, liposomes, gene guns, or by clustered regularly interspersed short palindromic repeats, or CRISPR, technology.

Biologically active proteins or polypeptides, or biologically active fragments, derivatives, or analogues thereof that may be introduced into the induced pluripotent stem cells, prior to the production of mesenchymal stem cells therefrom, include polynucleotides encoding various therapeutic agents including, but not limited to, anti-inflammatory or inflammation modulatory agents, such as TSG-6, anti-angiogenic agents, tumor necrosis factors, interleukins, growth factors, anti-clotting agents, bone morphogenic proteins (BMPs), such as BMP-2, hormones, such as insulin, anti-tumor agents, and negative selective markers. It is to be understood, however, that the scope of the present invention is not intended to be limited to any particular biologically active protein or polypeptide, or biologically active fragment, derivative, or analogue thereof.

In a non-limiting embodiment the at least one biologically active protein or polypeptide or biologically active fragment, derivative, or analogue is tumor necrosis factor alpha stimulating gene 6 (TSG-6) protein or a biologically active fragment, derivative, or analogue thereof.

In a non-limiting embodiment, the TSG-6 protein is the "native" TSG-6 protein, which has 277 amino acid residues as shown hereinbelow.

```
MIILIYLFLL LWEDTQGWGF KDGIFHNSIW LERAAGVYHR

EARSGKYKLT YAEAKAVCEF EGGHLATYKQ LEAARKIGFH

VCAAGWMAKG RVGYPIVKPG PNCGFGKTGI IDYGIRLNRS

ERWDAYCYNP HAKECGGVFT DPKQIFKSPG FPNEYEDNQI

CYWHIRLKYG QRIHLSFLDF DLEDDPGCLA DYVEIYDSYD

DVHGFVGRYC GDELPDDIIS TGNVMTLKFL SDASVTAGGF

QIKYVAMDPV SKSSQGKNTS TTSTGNKNFL AGRFSHL
```

In another non-limiting embodiment, the TSG-6 protein or biologically active fragment, derivative, or analogue thereof is a fragment of TSG-6 protein known as a TSG-6-LINK protein, or a TSG-6 link module domain. In one non-limiting embodiment, the TSG-6 link module domain consists of amino acid residues 1 through 133 of the above-mentioned sequence.

In another non-limiting embodiment, the TSG-6 link module domain consists of amino acid residues 1 through 98 of the above-mentioned sequence and is described in Day, et al., *Protein Expr. Purif.*, Vol. 8, No. 1, pgs. 1-16 (August 1996).

In another non-limiting embodiment, the TSG-6 protein or a biologically active fragment, derivative, or analogue thereof, has a "His-tag" at the C-terminal thereof. The term "His-tag", as used herein, means that one or more histidine residues are bound to the C-terminal of the TSG-6 protein or biologically active fragment, derivative, or analogue thereof. In another non-limiting embodiment, the "His-tag" has six histidine residues at the C-terminal of the TSG-6 protein or a biologically active fragment, derivative, or analogue thereof.

In a non-limiting embodiment, when the TSG-6 protein, or biologically active fragment, derivative, or analogue thereof, includes a "His-tag", at the C-terminal thereof, the TSG-6 protein or biologically active fragment, derivative, or analogue thereof, may include a cleavage site that provides for cleavage of the "His-tag" from the TSG-6 protein or biologically active fragment, derivative, or analogue thereof, after the TSG-6 protein, or biologically active fragment, derivative, or analogue thereof is produced.

In another non-limiting embodiment, the at least one biologically active protein or polypeptide, or biologically active fragment, derivative, or analogue thereof is a bone morphogenic protein, or BMP. In another non-limiting embodiment, the bone morphogenic protein is BMP-2 or a biologically active fragment, derivative, or analogue thereof.

In another non-limiting embodiment, the biologically active protein or polypeptide or biologically active fragment, derivative, or analogue thereof is a negative selective marker, which is capable of inhibiting, preventing, or destroying the growth of the genetically engineered mesenchymal stem cells if one desires to terminate a treatment with such genetically engineered mesenchymal stem cells.

In a non-limiting embodiment, the polynucleotide encoding the negative selective marker is under the control of an inducible promoter. Once the inducible promoter activates expression of the polynucleotide encoding the negative selective marker, the growth of the genetically engineered mesenchymal stem cells is inhibited, prevented, or destroyed. In a non-limiting embodiment, the negative selective marker is caspase 9.

In another non-limiting embodiment, the negative selective marker is a negative selective marker that reacts with a prodrug upon the administration thereof, whereby the growth of the genetically engineered mesenchymal stem cells is inhibited, prevented, or destroyed. In a non-limiting embodiment, the negative selective marker is Herpes Simplex Virus thymidine kinase. In another non-limiting embodiment, the prodrug which reacts with the Herpes Simplex Virus thymidine kinase to inhibit, prevent, or destroy the growth of the mesenchymal stem cells is ganciclovir.

In another non-limiting embodiment, the at least one polynucleotide encoding at least one biologically active protein or polypeptide or biologically active fragment, derivative, or analogue thereof is introduced into a "safe harbor" chromosomal locus in the induced pluripotent stem cells. In a non-limiting embodiment, the safe harbor chromosomal locus is the adeno-associated virus S1 (AAVS1) locus on human chromosome 19. In another non-limiting embodiment, the safe harbor chromosomal locus is located on human chromosome 13.

Thus, there are provided isolated genetically engineered mesenchymal stem cells derived from induced pluripotent stem cells as hereinabove described, including but not limited to genetically engineered human mesenchymal stem cells. The genetically engineered human mesenchymal stem cells may be administered in an amount effective to treat a variety of diseases, disorders and conditions, such as those hereinabove described, or regenerate a variety of cells, tissues, and organs such as those hereinabove described. The exact dosage of genetically engineered mesenchymal stem cells to be administered is dependent upon a variety of factors, such as the weight, height, age, and sex of the patient, the disease, condition, or disorder being treated, and the extent and severity thereof, or the particular cells, tissue, or organ to be regenerated.

The genetically engineered human mesenchymal stem cells of the present invention may be administered systemically, such as by intramuscular, intravenous, intraarterial, or intraperitoneal administration. Alternatively, the genetically engineered mesenchymal stem cells may be administered directly to the cells, tissues, or organs that are to be treated.

The genetically engineered human mesenchymal stem cells of the present invention may be administered in conjunction with any pharmaceutically acceptable carrier or excipient or adjuvant known to those skilled in the art.

In accordance with another aspect of the present invention, there is provided a kit for determining the presence and/or amount of at least one RNA sequence encoding a protein in mesenchymal stem cells. The kit comprises a preparation of mesenchymal stem cells that produce a predetermined amount of at least one RNA sequence encoding a protein. The kit also comprises at least two identical culture media for culturing and expanding mesenchymal stem cells and instructions for culturing and expanding the mesenchymal stem cells.

Also included in the kit are at least two identical sets of reagents for extracting RNA from mesenchymal stem cells and instructions for extracting RNA from the mesenchymal stem cells. The kit further comprises at least three microplates suitable for conducting reverse transcripts PCR, or RT-PCR of RNA.

The kit also contains a predetermined amount of at least one RNA sequence encoding a protein. The predetermined amount(s) of the at least one RNA sequence(s) encoding a protein was (were) extracted previously from the mesenchymal stem cells hereinabove described. The predetermined amount(s) of the at least one RNA sequence(s), in a non-limiting embodiment, is (are) pre-loaded onto at least one of the at least three microplates suitable for conducting reverse transcription PCR of the RNA.

The kit also includes a 3' DNA primer and a 5' DNA primer corresponding to each of the at least one RNA sequence(s) encoding a protein of which the presence and/or amount thereof is to be determined.

The kit further includes at least two identical sets of reagents for conducting reverse transcription PCR.

Furthermore, the kit includes instructions for conducting reverse transcription PCR of RNA, and instructions for assaying for the presence and or amount of each of the at least one RNA sequence encoding a protein.

The mesenchymal stem cells that produce a predetermined amount of at least one RNA sequence encoding a protein can be obtained from any animal, including human and non-human animals, and any tissue or other cellular source in which mesenchymal stem cells are present. In a non-limiting embodiment, the mesenchymal stem cells are obtained from a human. In another non-limiting embodiment, the mesenchymal stem cells are obtained from human bone marrow. In another non-limiting embodiment, the mesenchymal stem cells are produced from induced pluripotent stem cells.

In a non-limiting embodiment, the mesenchymal stem cells contained in the kit are supplied as a frozen vial to be stored under liquid nitrogen. Each vial contains 0.75 to 1.0 million cells in 1 ml of α-minimum essential medium (α-MEM) (Gibco), 5% dimethylsulfoxide (DMSO), and 20% fetal bovine serum (Atlanta Biologicals).

The culture media used for culturing and expanding the mesenchymal stem cells may be any culture media known to those skilled in the art for culturing and expanding mesenchymal stem cells. In a non-limiting embodiment, the kit contains at least two identical samples of culture media in an amount of about 100 ml.

In a non-limiting embodiment, the at least two identical samples of culture media contain complete culture medium (CCM) consisting of α-minimum essential medium (α-MEM) supplemented with 17% fetal bovine serum (FBS, Atlanta Biologicals), 100 units/ml penicillum (Gibco), 100 µg/ml streptomycin (Gibco), and 2 mM L-glutamine (Gibco).

The instructions for culturing and expanding the mesenchymal stem cells in general direct one to culture and expand the mesenchymal stem cells under conditions and for a period of time sufficient to provide an amount of mesenchymal stem cells from which a sufficient amount of RNA can be extracted from the cells. In a non-limiting embodiment, the instructions direct one to culture the mesenchymal stem cells in the medium for a total period of time of from about 6 days to about 8 days.

In a non-limiting embodiment, the instructions instruct one skilled in the art to thaw the frozen vials of the mesenchymal stem cells at 37° C., and then suspend the mesenchymal stem cells in 100 ml of the complete culture medium (CCM). The instructions then instruct one to plate the cells on a 152 cm$^2$ culture dish (Corning), and then to wash the cells with phosphate buffered saline, and to harvest adjacent cells by exposure to 0.25% trypsin and 1mM ethylenediaminetetracetic acid (EDTA) (Gibco) for 2 to 7 minutes. The instructions then instruct one to plate the cells in 100 ml CCM at 200 cells/cm$^2$, replace the medium after 3 days, and lift the cells with 0.25% trypsin and 1 mM EDTA after 5 days.

The RNA may be extracted from the mesenchymal stem cells with any reagents for extracting RNA from cells that are known to those skilled in the art. In a non-limiting embodiment, the kit includes a "sub kit" that contains the reagents and other materials for extracting RNA from cells. An example of such a "sub-kit" is the RNeasy Mini Kit, sold by Qiagen Inc. Such "sub-kit" also contains appropriate instructions for extracting RNA from cells. In another non-limiting embodiment, the "sub-kit" is the High Pure RNA Isolation Kit (catalog no. 11828665001, Roche).

The microplates which are contained in the kit may be any microplates known to those skilled in the art to be suitable for conducting reverse transcriptase PCR of RNA.

The 3' and 5' DNA primers contained in the kit may any 3' and 5' DNA primers that are appropriate for reverse transcription PCR. The sequences of such primers are determined in part by the RNA sequences that one wishes to detect.

The reagents for conducting reverse transcription PCR may be any of those known to one skilled in the art, including reverse transcriptase, dATP, dGTP, dCTP, and dTTP.

In a non-limiting embodiment, the microtiter plates, 3' and 5' primers, and reagents are supplied as the Custom Profiler RT 2 PCR Array (www.sasciences.com), which includes the microtiter plates preloaded with the appropriate 3' and 5' DNA primers, and the reagents to develop the reverse transcription PCR reactions, The reverse transcription PCR is conducted in accordance with the instructions provided in the kit. Such instructions will direct one to conduct the reverse transcription PCR according to any of a variety of procedures known to those skilled in the art. Examples of such procedures may be contained in the Custom Profiler RT2 PCR Array, or may be those described in Wu, et al., Methods in Gene Biotechnology, CRC Press (1997), pgs. 16-21.

The kit contains means for determining the presence and/or amount of each at least one RNA sequence encoding a protein, plus instructions for using such means. Such means may be any of those known to those skilled in the art. Examples of such means includes, but are not limited to Sequence Detection Software V2.3 (Life Technologies) and the comparative CT method using RQ manager V1.2 (Life Technologies).

The kit of the present invention may be used to detect any of a variety of RNA sequences encoding proteins in mesenchymal stem cells. Such proteins include, but are not limited to Nanog, Oct. 4, Ecad, Foxa2, the epitopes CD73, CD105, CD166, CD44, CD90, HLA-DR, CD11b, CD24, CD34, and CD45, the mesodermal marker CD140A, VEGF, ILR1, mPGES1, IL-6, TGFBR2, ID3, SDF1, HAS1, and HAS2. It is to be understood, however, that the scope of the present invention is not to be limited to the detection of any specific RNA sequence or RNA sequences encoding specific proteins. In fact, in a non-limiting embodiment, the kit of the present invention may be used to detect the presence and/or amount of 100 or more RNA sequences encoding 100 or more proteins in mesenchymal stem cells.

The kit of present invention is applicable particularly to determining the presence and/or amount of at least one RNA sequence encoding a protein in a test population of mesenchymal stem cells from any source and obtained by any procedure known to those skilled in the art Parallel experiments are conducted in which the test population of mesenchymal stem cells and the population of mesenchymal stem cells producing a predetermined amount(s) of RNA sequence(s) encoding a protein(s) are cultured and expanded. RNA then is extracted from both populations of cells, and reverse transcription PCR is conducted on both of the extracted RNAs. Reverse transcription PCR also is conducted on the predetermined amount of RNA sequences previously extracted from the mesenchymal stem cells producing the predetermined amounts of RNA sequence(s) in order to verify the accuracy of the experiments. Then, the presence and/or amount(s) of RNA sequence(s) produced by the test population of mesenchymal stem cells is compared with the amount(s) of RNA sequence(s) produced by the mesenchymal stem cells that produce a predetermined amount(s) of such RNA sequence(s). Through such a comparison, one can determine whether the test population of mesenchymal stem cells is suitable for a variety of therapeutic applications.

BRIEF DESCRIPTION OF THE DRAWINGS

The invention now will be described with respect to the drawings.

Figure 1A:
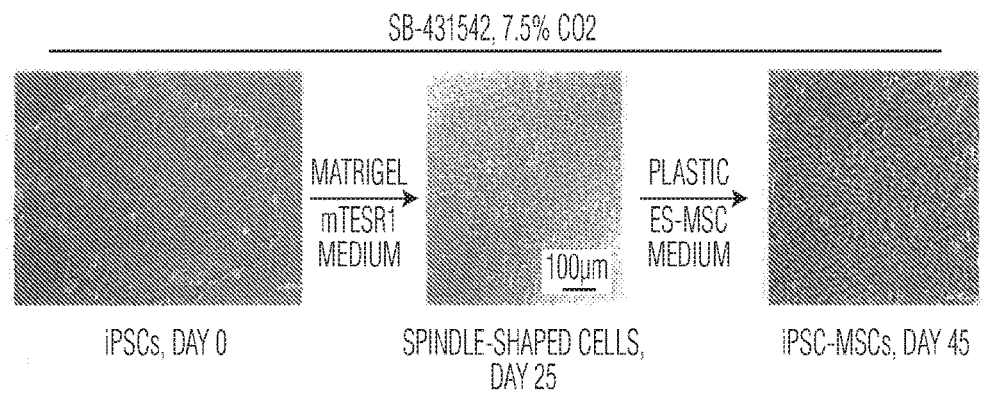
FIG. 1. Characterization of iPSC-MSCs.
(A) Derivation and morphology of MSC-like cells from human iPSCs. (B) qRT-PCR analysis of relative expression of marker genes for pluoripotency and each germ layer in iPSCs, BM-MSCs and iPSC-MSCs (**: $P<0.01$ vs. iPSCs, ND: not detected). (C) Flow cytometry analysis of surface markers in iPSC-MSCs. (D-F) Multi-lineage differentiation of iPSC-MSCs. (G) Telomerase activities in iPSCs, BM-MSCs and iPSC-MSCs. (H) CFU-F forming assay. *; $P<0.05$. (I) Growth curves of BM-MSCs and iPSC-MSCs (n=3). iPSC-MSCs ceased expanding after 17 passages (64 population doublings) and BM-MSCs after 16 passages (48 population doublings). (J) Karyotype of iPSC-MSCs at passage 7. (Wi Cell Cytogenetics Lab).

(C) qRT-PCR analysis of LOX in cancer cells cultured alone or with MSCs for 3 days.

EXAMPLES

The invention now will be described with respect to the examples; however, the scope of the present invention is not intended to be limited thereby.

Example 1

Experimental Procedures
iPSC Culture and Differentiation to MSCs

Blood cell derived human iPS cell line CY2 was generated with episomal plasmids (Yu et al., 2009), completely free of vector and transgene sequences, and obtained from Center for Regenerative Medicine in National Institutes of Health. The cells were maintained and expanded in Matrigel-coated plates in a feeder-free medium mTeSRI (STEMCELL Technologies). As an initial step for derivation of MSCs, iPSCs were cultured in the mTESRI feeder-free medium supplemented with 10 µM TGFβ inhibitor SB-431542 (Sanchez et al., 2011) (Sigma-Aldrich, MO) in Matrigel-coated plates at 370 C, 7,5% $CO_2$ (Olivier and Bouhassira, 2011) and passaged at 80-90% confluence by 2 mg/ml of Dispase. When most cells at the edge of cell cluster became spindle-shaped in about 25 days, they were trypsinized into single cells and cultured in standard tissue culture plastic dishes with modified human ES-MSC medium (Knockout-DMEM containing 10% knockout serum replacement, nonessential amino acids, penicillin-streptomycin, glutamine, and (β-mercaptoethanol, and 10 ng/ml of bFGF) (Lai et al., 2011) in the presence of SB-431542. The medium was changed daily and the cells were passaged at 80-90% confluence at the ratio of 1:3 about every 3 days, and analyzed for expression of MSC surface markers by flow cytometry weekly. After 21 days, the majority of cells was positive for MSC surface markers (>90%) and negative for non-MSC markers (<5%), and were named passage 0 iPSC-MSCs. Then these iPSC-MSCs were seeded at a density of 500 cells per cm2 growth area in 20% FBS α-MEM medium, and harvested at 70-80% confluence for further experiments. The bone marrow MSCs (donor #7075L) were from our NIH-funded MSC distribution center (http://medicine.tamhsc.edu/irm/msc-distribution.html) and cultured under the same condition of iPSC-MSCs. The BM-MSCs were expanded to passage 4 and 70% confluency for most experiments unless specified otherwise. The multi-lineage differentiation of iPS-MSCs was performed using standard published conditions for BM-MSCs (Gregory and Prockop, 2007).

Quantitative RT-PCR Analysis

Quantitative RT-PCR (qRT-PCR) was done as reported (Hai et al., 2010). The sequences of primers were retrieved from Primerbank (http://pqa.mqh.harvard.edu/primerbank/) and synthesized by Invitrogen.

Telomerase and Colony-Forming Unit-Fibroblasts Assay

Telomerase activity was measured with a Quantitative Telomerase Detection Kit (Allied Biotech, Cat. MT3010). Colony-forming unit-fibroblasts (CFU-F) culture assays were performed as reported previously (Shangguan et al., 2012).

Transwell Cell Migration or Invasion Assay

Migration of MSCs toward 293T or MDA-MB-231 cancer cells in vitro was examined as reported previously (Shangguan et al., 2012). For invasion assay, cancer cells were transduced with lentiviruses carrying CMV-copGFP (System Biosciences, MOI=10), cultured alone or co-cultured with equal numbers of BM- or iPSC-MSCs for 3 days in 20% FBS a-MEM medium, isolated by FACS and then seeded onto the top of 24-well transwell insert with 50,000 cells/well and allowed to invade overnight across 8-µm porous membranes coated with collagen IV toward media with 10% FBS in the bottom chamber. The membranes were fixed subsequently with 4% paraformaldehyde (PFA). The cells attached to the topside of the membrane were removed with a cotton swab, and the invaded cells on the reverse side of the membrane were stained with 1% crystal violet and counted (five random fields per well, triplicate wells) at 10× magnification under microscope (Nikon Eclipse 80i).

In Vivo Homing Assay

Subcutaneous xenograft models of LoVo colorectal cancer and MDA-MB-231 breast cancer were generated by inoculation of $1 \times 10^5$ LoVo cells or $1 \times 10^6$ MDA-MB-231 cells into NOD/SCID mice. When tumors reach 100 $mm^3$ as calculated by $(\pi \times length \times width^2)/6$ (Wapnir et al., 2001), $0.5 \times 10^6$ BM-MSCs or iPSC-MSCs transduced with CMV-copGFP lentiviruses (MOi=10) were injected via tail vein, and the primary tumor was harvested after 16 hours. Three pieces of sample of about 20 mg from the periphery, paracentral region or center of each tumor were collected to extract genomic DNA (gDNA) with the DNeasy Blood & Tissue kit (Qiagen), and 100 ng gDNA per well was used for qPCR of CMV promoter with customized Taqman assay (Life Technologies) as reported (Moulay et al., 2010). qPCR assay for human and mouse genes for GAPDH was used to normalize the gDNA loading as reported (Lee et al., 2009a). The standard curve was made with 100 ng gDNA from LoVo or MDA-MB-231 xenografts containing 800, 400, 200, 100, 50 and 0 pg gDNA isolated from the same patch of MSCs transduced with CMV-copGFP for infusion. The data from three samples of the same tumor were averaged to estimate the percentage of gDNAs from homed MSCs in all tumor gDNAs. Cryosections of tumors were stained for TurboGFP (Evrogen, Russia, AB514, 1:200).

Mammosphere Assay

Breast cancer cells were transduced with lentiviruses carrying CMV-copGFP, cultured alone or with BM-MSCs or iPSC-MSCs for 3 days, isolated by FACS, and then suspended at a density of 500 cells/well in ultra-low attachment 12-well plates. Cells were incubated for 7 days in the presence of corresponding MSC-conditioned medium and then the numbers of mammospheres were counted under microscopy.

EIA and ELISA

The levels of PGE2 and hyaluronan acid in supernatants of cell culture were determined with corresponding EIA kit (GE healthcare) and ELISA kit (R&D Systems).

Tumor Initiating Assay $5 \times 10^4$ or $1 \times 10^4$ HCC1806 breast cancer cells were injected alone or with $2 \times 10^5$ BM-MSCs or iPSC-MSCs into the $4^{th}$ mammary fat pad of NOD/SCID mice. The size of tumor was monitored every two days as above for 6 weeks.

Statistics

Statistical analysis was done with ANOVA using GraphPad Prism 5 (GraphPad Software). All in vitro experiments were done in triplicate unless specified. $P<0.05$ was considered statistically significant.

Results
Derivation of MSC-Like Cells from Human iPS Cells.

Figure 1B:
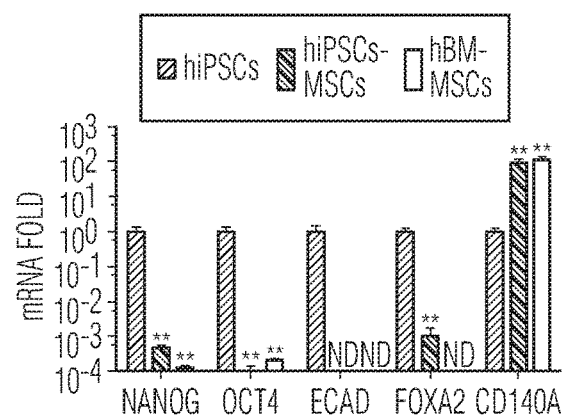
Figure 1C:
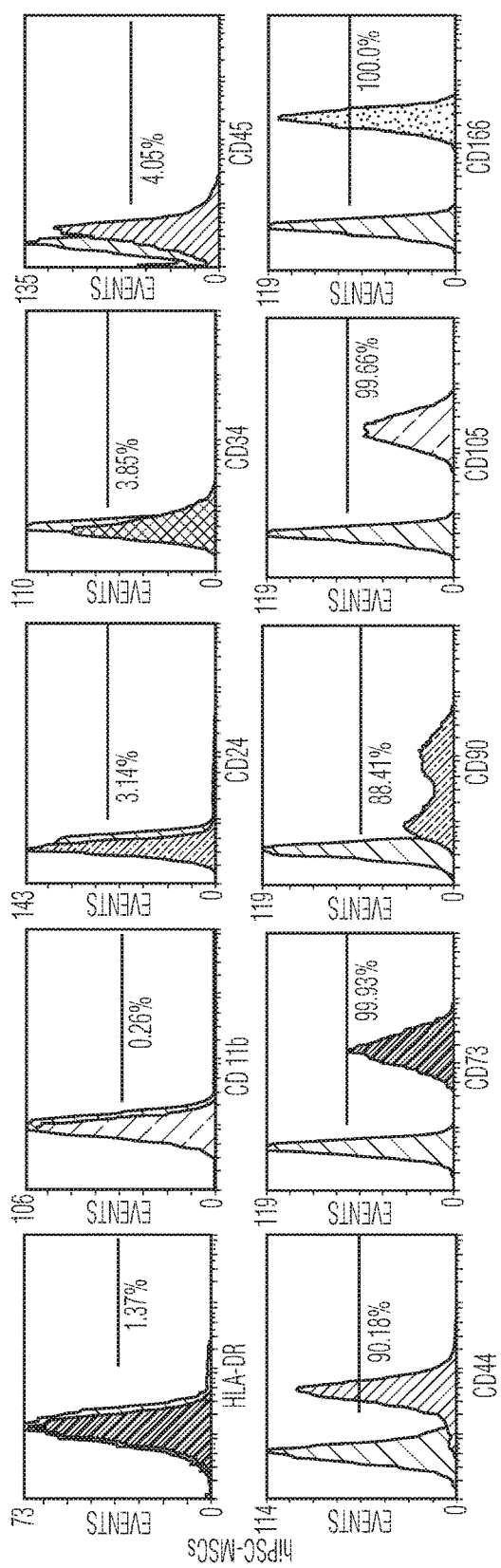
Figure 1D:
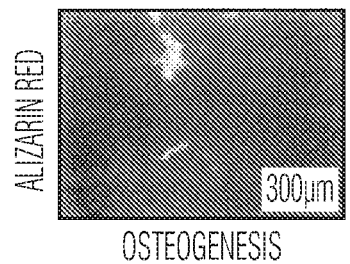
Figure 1E:
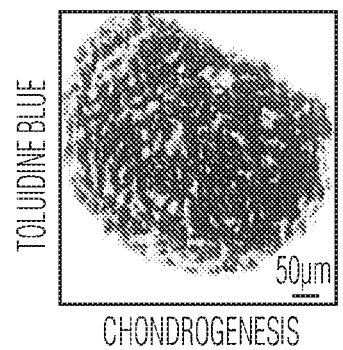
Figure 1F:
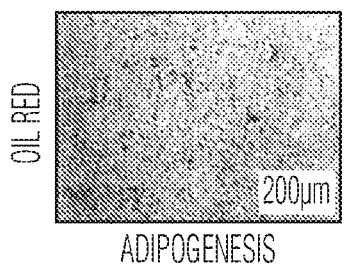
Figure 1G:
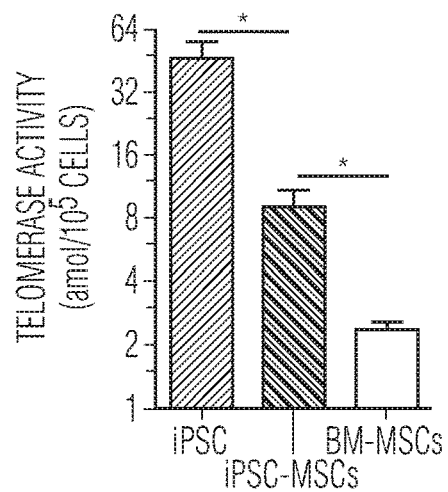
Figure 1H:
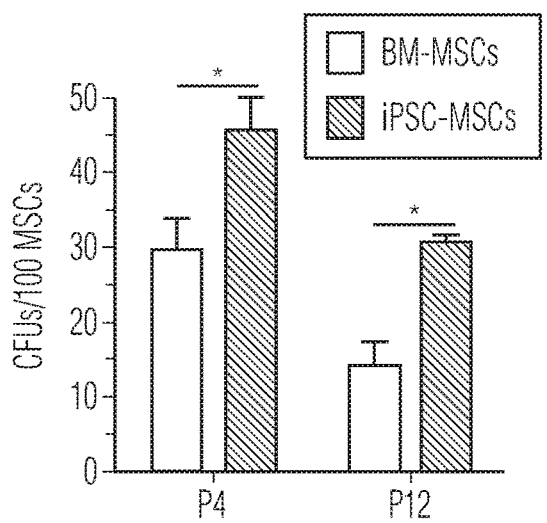
Figure 1I:
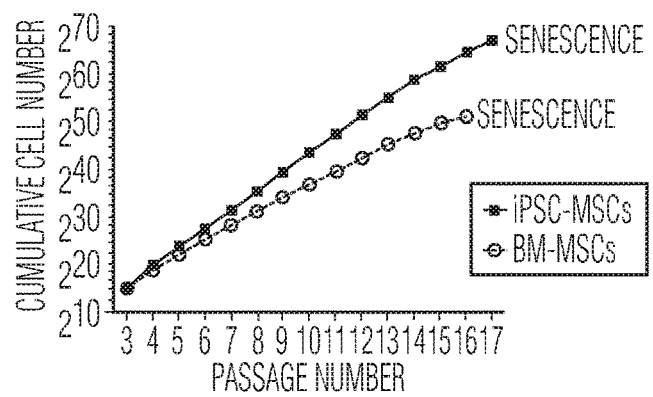
Figure 1J:
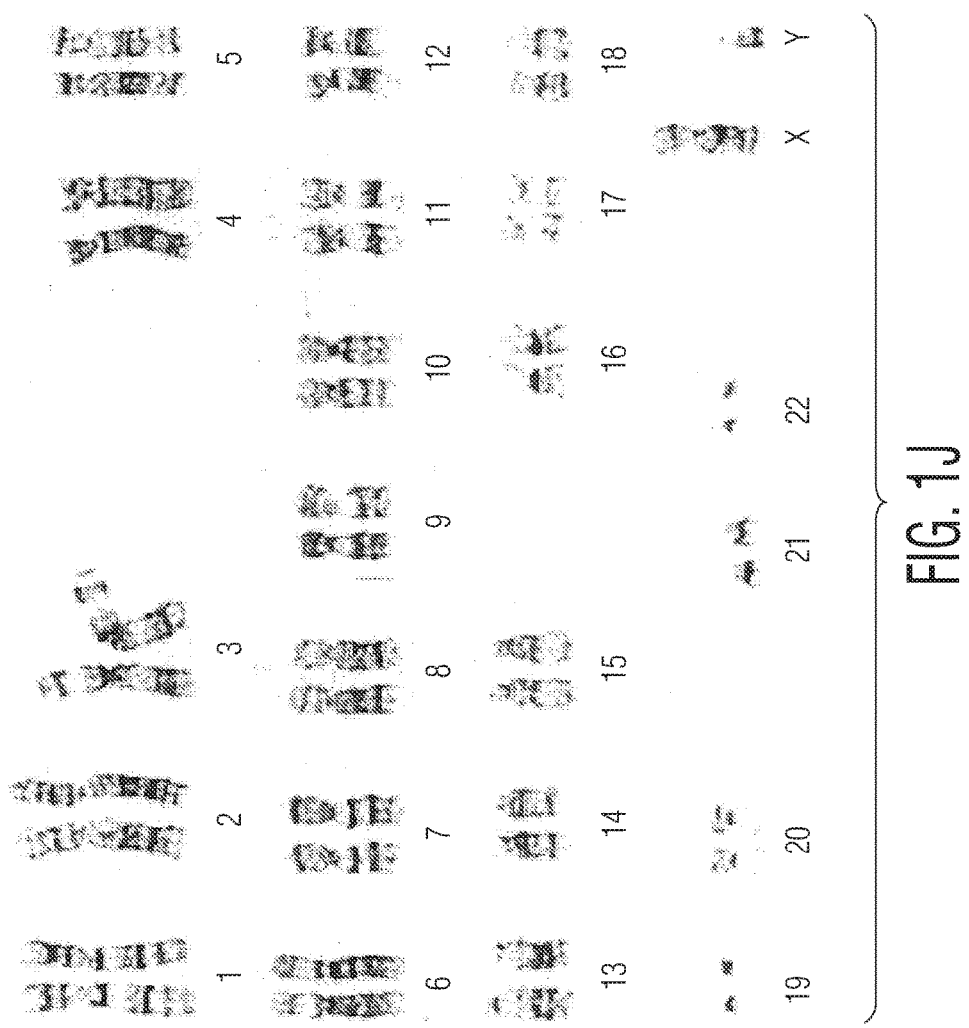

Sanchez et al. (2011) reported that inhibition of SMAD-2/3 signaling promoted derivation of MSCs from human ESCs but not from human iPSCs. To derive MSCs efficiently from human iPSCs, we modified their method by using chemically defined mTeSRI medium (Ludwig et al., 2006) supplemented with the SMAD-2/3 inhibitor (SB-431542), and an atmosphere of 7.5% $CO_2$ (Olivier and Bouhassira, 2011) to culture colonies of cells on Matrigel-coated plates. The cells were passaged at 80-90% confluency by lifting with Dispase. After about 25 days most cells became larger with increased cytoplasm and cells at the edge of cell cluster became spindle-shaped, suggesting spontaneous differentiation (FIG. 1A). Then we digested the cultures with trypsin to generate suspensions of single cells and transferred them to standard tissue culture plates. The cells were incubated in ES-MSC medium (Lai et al., 2011) containing SB-431542, lifted at 80 to 90% confluency by trypsin about every 3 days, diluted 1:3, and passaged repeatedly under the same conditions (Lian et al., 2007). During repeated passaging by trypsinization, more and more adherent cells gradually showed spindle-like morphology and appeared in whorls similar to MSCs and fibroblasts (FIG. 1A). After 45 days, there was a marked decrease in the adherent cells of expression of pluripotent genes Nanog and Oct4, the neuroectoderm marker Ecad, and the endoderm marker Foxa2. In contrast, there was a marked increase in the expression of the mesodermal marker CD140A/Pdgfra (FIG. 1B, $P<0.001$). Flow cytometry analysis indicated almost all adherent cells (>99.6%) expressed putative MSC markers CD73, CD105 and CD166, and the vast majority of adherent cells (>88.4%) also expressed the other MSC markers CD44 and CD90. Only a very small fraction of these cells expressed the negative MSC markers including HLA-DR, CD11b, CD24, CD34 and CD45 (<4.1%, FIG. 1C). When incubated in standard osteogenic media, the adherent cells were remarkably osteogenic, generating a fully differentiated monolayer of mineralizing MSCs within 10 days, about half of the time required for BM-MSCs (FIG. 1D). The adherent cells also generated cartilage in micromass cultures in the presence of both BMP2 and TGFβ (FIG. 1E). In contrast, when the cells were exposed to routine adipogenic conditions for a standard duration of 20 days, the cells modestly responsive compared to BM-MSCs (FIG. 1F). Because the adherent cells met the standard criteria of MSCs (Dominici et al., 2006), they were referred to subsequently as iPSC-MSCs and designated as passage 0. As expected, telomerase activity in iPSC-MSCs was much higher than that in BM-MSCs (passage 4) but much lower than that in parent iPSCs (passage 39) (FIG. 1G, $P<0.05$). Consequently, the CFU-F forming efficiency of iPSC-MSCs also was much higher than that of BM-MSCs at passage 4 and 12 (FIG. 1H, $P<0.05$), indicating better expandability of iPSC-MSCs compared to BM-MSCs. The average population doubling time from passage 3 to 15 for iPSC-MSCs was significantly shorter than that of BM-MSCs (25.28±2.92 vs. 33.91±5.03 hours, n=3, $P<0.05$), indicating that iPSC-MSCs propagate more rapidly than BM-MSCs; however, iPSC-MSCs were not immortal in culture. They underwent senescence and could not be expanded beyond 17 passages (64 population doublings), similar to BM-MSCs cultured under the same condition that underwent senescence after 16 passages (48 population doublings) (FIG. 1I). Cytogenetic analysis indicated that iPSC-MSCs at passage 7 had a normal karyotype (FIG. 1J), and no teratoma formation was observed in NOD/SCID mice inoculated with iPSC-MSCs for 4 months. The data indicated therefore that we developed an efficient and safe protocol to derive MSCs from human iPS cells.

Human iPSC-MSCs were Capable of Homing to Tumors.

Figure 2A:
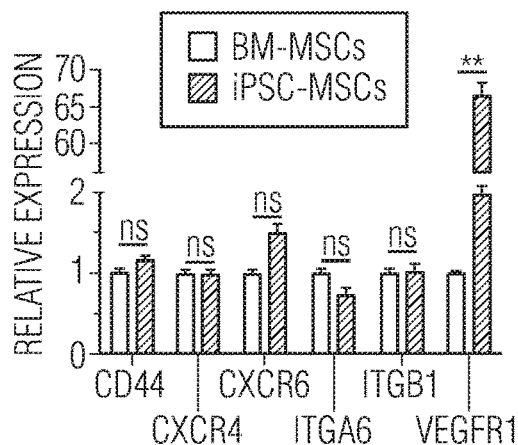
FIG. 2. The Tumor Tropism of IPSC-MSC.
(A) qRT-PCR analysis of genes related to tumor homing in MSCs. (B) In vitro migration of MSCs toward 293T or MDA-MB-231 cells in a transwell. (C) Standard curve for qPCR assays of MSCs carrying CMV-copGFP added into LoVo or MDA-MB-231 cancer xenografts. Values indicate ACt for primers for CMV promoter and mouse/human GAPDH genes on same samples, n=3. (D, E) Estimated percentage of homed MSCs carrying CMV-copGFP in all tumor cells in the LoVo or MDA-MB-231 cancer xenograft model based on qPCR of CMV promoter, n=5. (F) Homing of intravenously infused GFP-MSCs to established subcutaneous LoVo or MDA-MB-231 cancer xenografts was confirmed by immunofluorescence staining of copGFP.
Figure 2B:
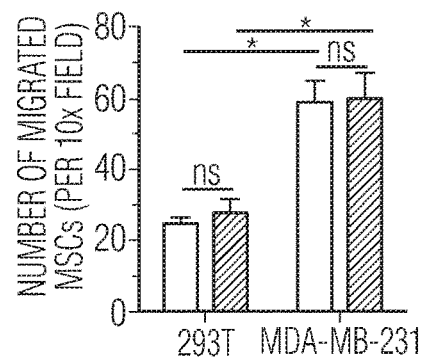
Figure 2C:
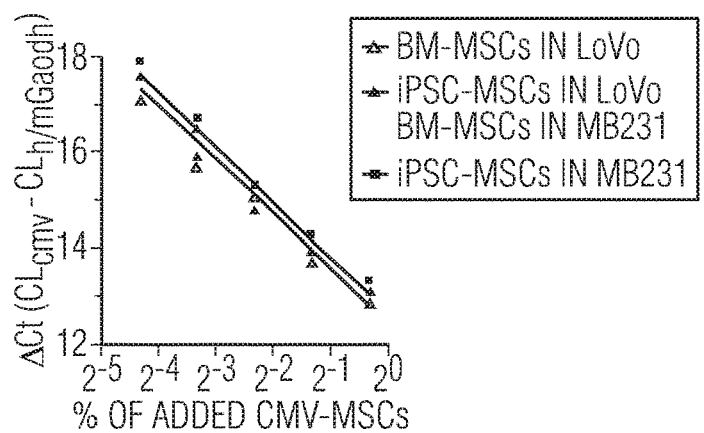
Figure 2D:
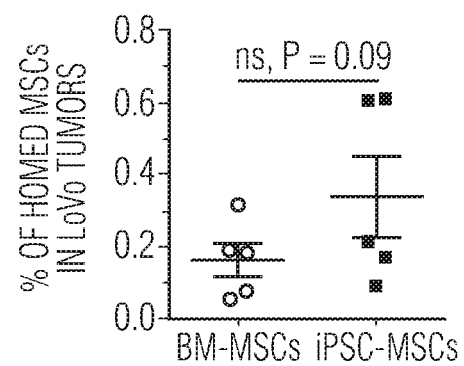
Figure 2E:
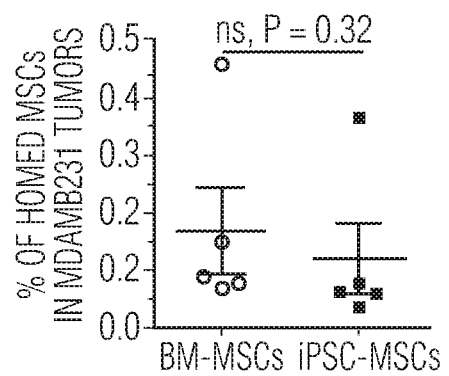
Figure 2F:
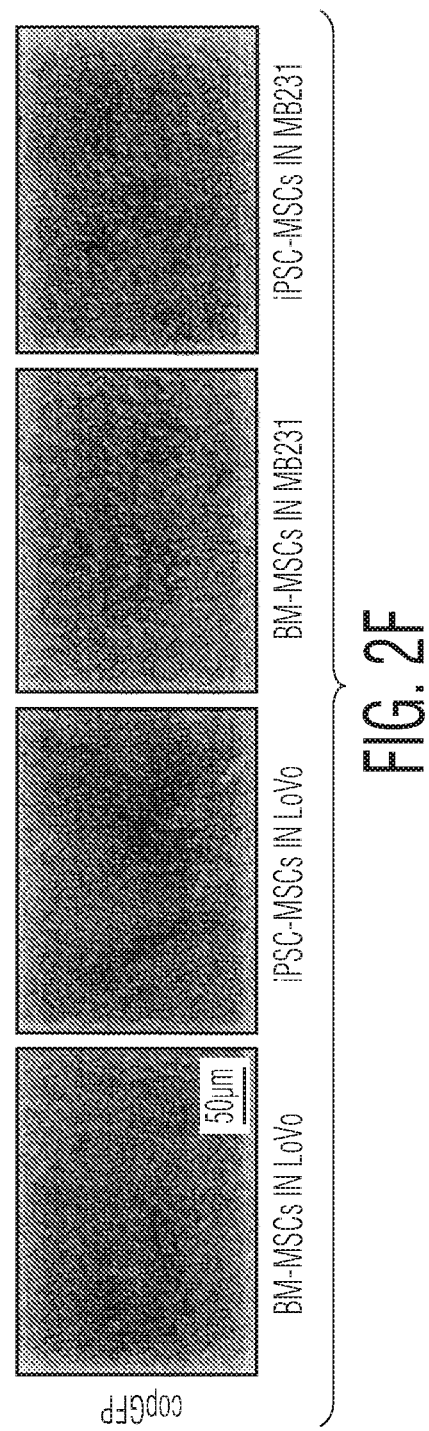

MSCs from various tissues have a unique tumor-homing capacity that enables them to serve as vehicles for gene therapy of advanced cancers. The tumor tropism of these MSCs is mediated by multiple chemokine receptors such as CXCR4 and CXCR6 (Jung et al., 2013; Quante et al., 2011; Song and Li, 2011), CD44 (Spaeth et al., 2013), VEGFR1 (Chaturvedi et al., 2013), and integrins such as ITGA6 and ITGB1 (Ip et al., 2007; Lee et al., 2009b). The expression of VEGFR1 was dramatically higher in iPSC-MSCs than that in BM-MSCs, whereas the expression of other homing-related genes was comparable between iPSC-MSC and BM-MSCs (FIG. 2A). In vitro transwell migration experiments showed that there was significantly increased migration of BM-MSCs to MDA-MB231 cells, a line of triple-negative human breast cancer cells, as compared to control human embryonic kidney 293T cells. Similar results were reported previously (Loebinger et al., 2009). The migration of iPSC-MSCs to MDA-MB231 cells was similarly significantly increased compared with that to 293T cells or medium alone (FIG. 2B, $P<0.01$), and was comparable to that of BM-MSCs to the MDA-MB231 cells ($P>0.1$). To confirm the in vivo tumor tropism of iPSC-MSCs, we generated human cancer xenograft models of LoVo colorectal cancer cells and MDA-MB231 breast cancer cells. After establishment of tumor, BM-MSCs or iPSC-MSCs transduced with CMV-copGFP lentivirus were injected into tumor-bearing mice intravenously. To quantify the homing of MSCs to cancer, we developed individual standard curves of CMV qPCR for BM-MSCs or iPSC-MSCs carrying CMV-copGFP by adding varying amounts of gDNAs from corresponding cells to gDNAs of LoVo or MDA-MB-231 tumor tissues from mice without infusion of MSCs (FIG. 2C, $R2>0.97$). Sixteen hours after MSC infusion, qPCR of CMV promoter sequence indicated that infused BM-MSCs and iPSC-MSCs homed to LoVo or MDA-MB-231 tumors with comparable efficiencies (FIG. 2D, E, $P>0.05$), Consistent with these observations, GFP+ cells were found in sections of LoVo or MDA-MB-231 tumor samples from mice infused with BM-MSCs or iPSC-MSCs carrying CMV-copGFP (FIG. 2F). Taken together, these data indicated that iPSC-MSCs are capable of homing to cancer similar to BM-MSCs.

iPSC-MSCs had Less Potential than BM-MSCs to Promote Epithelial-mesenchymal Transition, Invasion and Cancer Stem Cell Expansion.

Figure 3A:
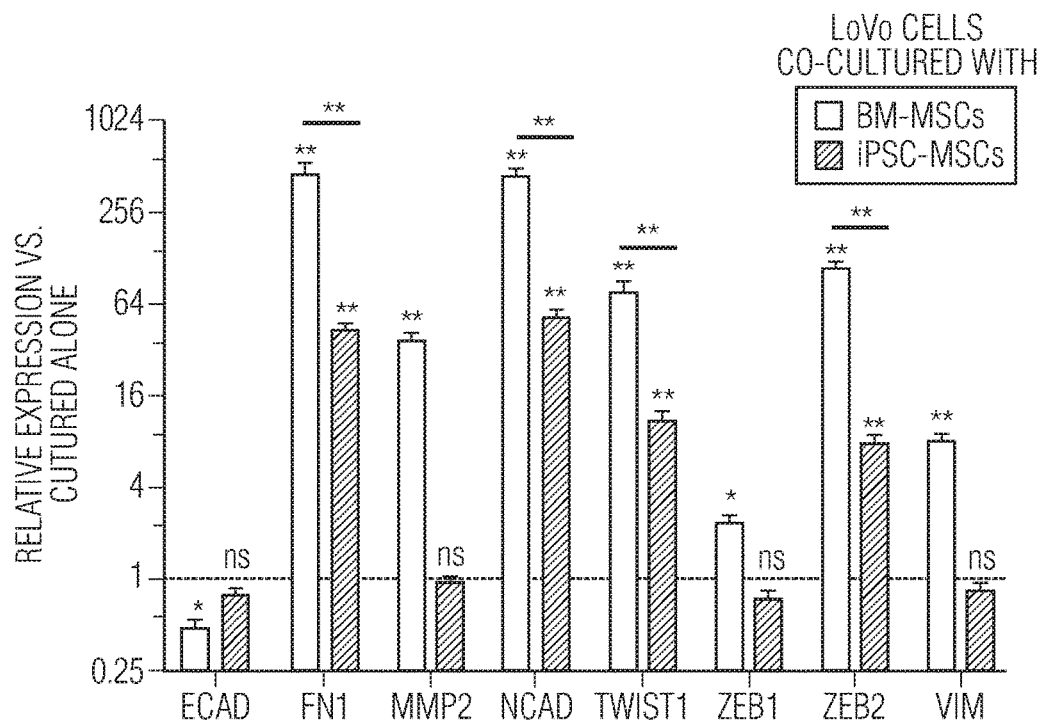
FIG. 3. The effects of iPSC-MSC on EMT, invasion and cancer stem cells of co-cultured cancer cells.
(A-C and E) After co-culture with GFP-labeled BM-MSCs or iPS-MSCs, cancer cells were isolated by FACS and subjected to (A) qRT-PCR analysis of genes related with EMT and invasion, (B) invasion assay with collagen IV coated Boyden chambers, (C) The representative flow cytometry analysis of ALDH+population and the percentage of ALDH+ cells (mean±SEM of 3 independent tests), (D) effects of iPSC-MSCs co-culture on HCC1806 breast cancer cells as shown by the expression of EMT-related genes analyzed by qRT-PCR (top panel) and the representative flow cytometry analysis of ALDH$^+$ population and the percentage of ALDH$^+$ cells (mean±SEM of 3 independent tests) (bottom panel) (E) the mammosphere forming assay of breast cancer cells. (F) Sizes (weights) of tumors derived from HHC1806 cells injected into SCID mice with BM- or iPSC-MSCs.
Figure 3B:
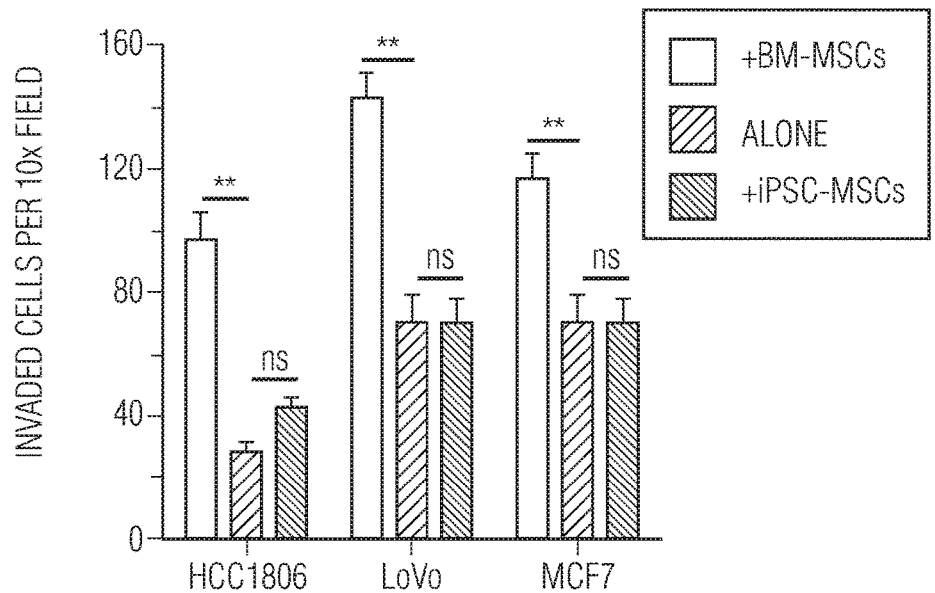
Figure 3C:
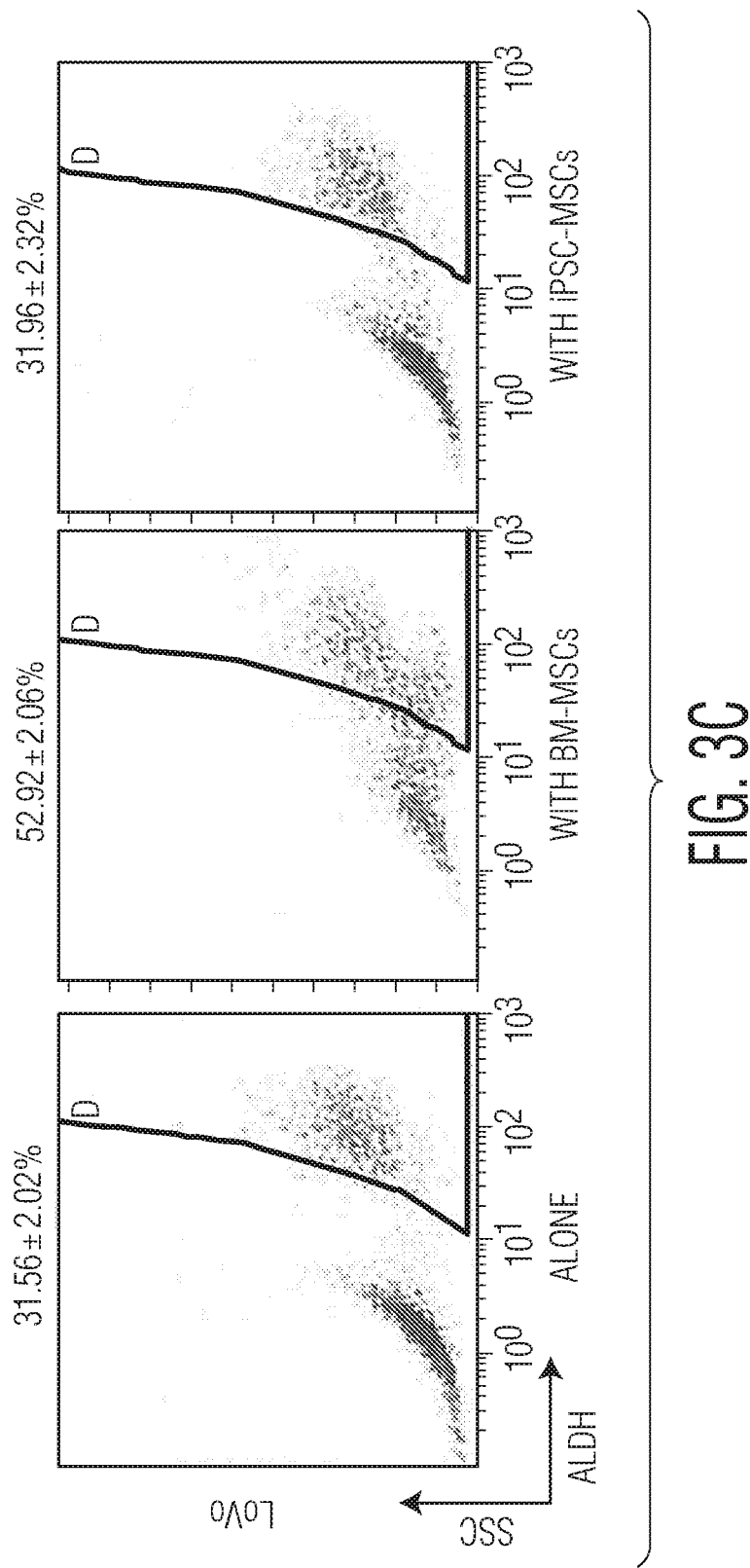
Figure 3D:
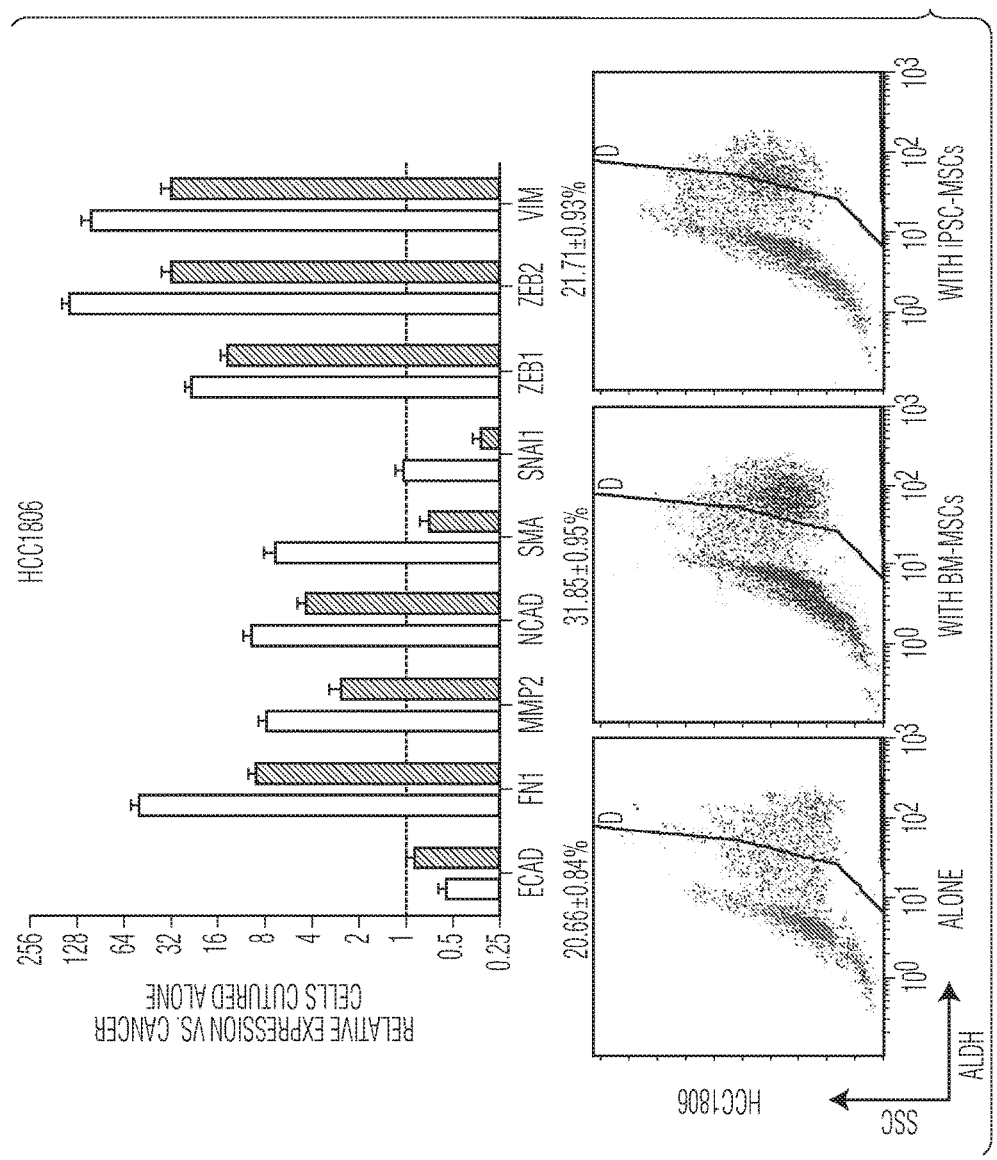
Figure 3E:
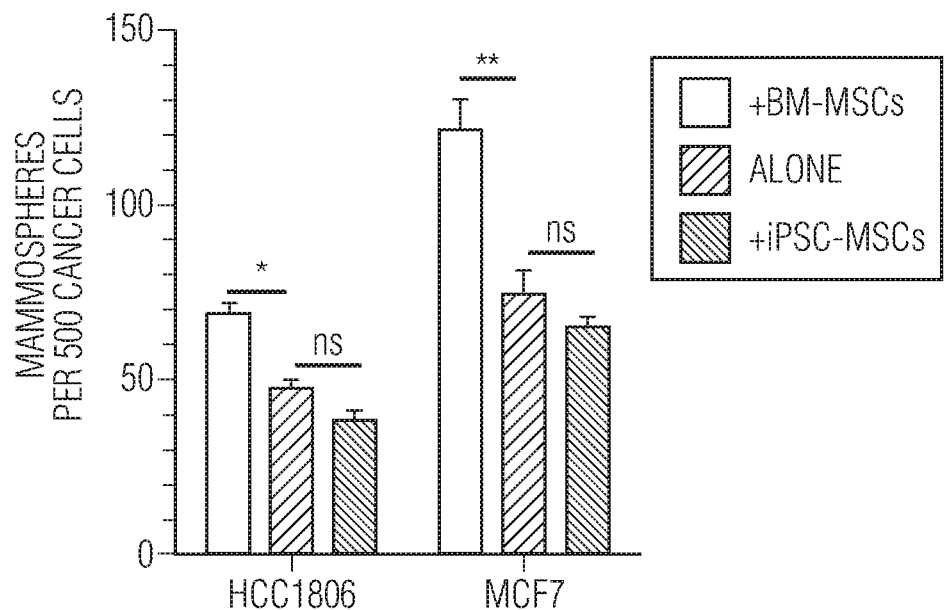
Figure 3F:
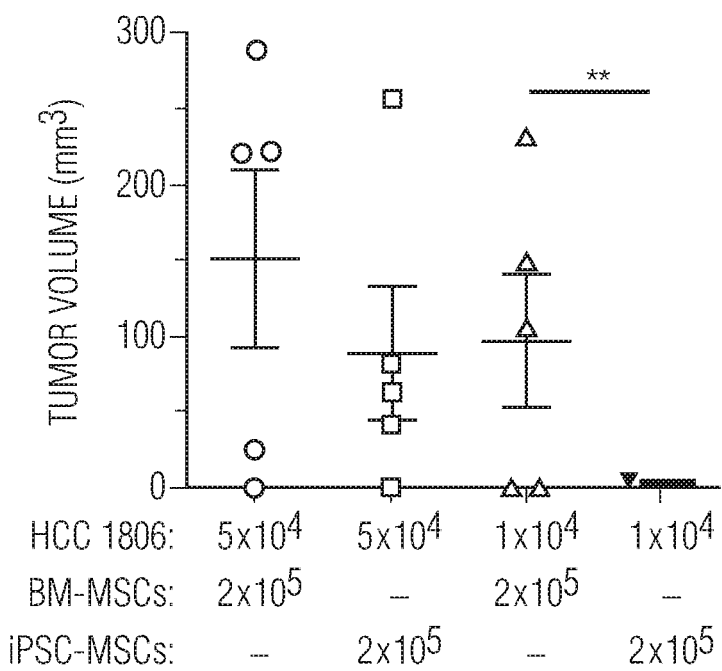

Interactions between carcinoma cells and MSCs promote metastasis and/or expansion of the cancer stem cells by enhancing epithelial-mesenchymal transition (EMT) (Li et al., 2012). We first compared the potential of iPSC-MSCs and BM-MSCs to enhance EMT of co-cultured cancer cells. Cancer cells were transduced with CMV-copGFP lentiviruses and sorted by FACS after co-culture with MSCs. In LoVo cancer cells, 12 hours of co-cultures with BM-MSCs significantly decreased the expression of the epithelial maker E-cadherin (ECAD) and significantly increased expression of mesenchymal makers fibronectin1 (FN1), N-cadherin (NCAD), vimentin (VIM) and metalloproteinase 2 (MMP2) and pro-EMT factors ZEB1, ZEB2 and TWIST1 (FIG. 3A). In contrast, co-culture with iPSC-MSCs did not decrease expression of ECAD significantly and had either no significant effects on or produced much smaller increases of the expression of these mesenchymal markers or pro-EMT genes in LoVo cells (FIG. 3A). The results demonstrated therefore that the iPSC-MSCs had less potential to promote EMT than BM-MSCs. To determine whether the iPSC-MSCs promoted invasion of cancer cells, an invasion assay using collagen IV-coated Boyden chambers was used. After co-culture with BM-MSCs for 3 days, invasion of LoVo, HCC1806 and MCF7 human cancer cells was increased significantly (FIG. 3B, $P<0.05$). In contrast, there was no significant increase after co-culture with iPSC-MSCs (FIG. 3B, P>0.05). To test whether the iPSC-MSCs promoted expansion of cancer stem cells, we used an assay of the ALDH+population of LoVo colorectal cancer cells, the putative cancer stem cells. After co-culture with BM-MSCs for 5 days, there was significant expansion of the ALDH+ cells (FIG. 3C). Co-culture with iPSC-MSCs had no significant effect. Similar effects of iPSC-MSCs on expression of EMT-related genes and ALDH+ population were observed in HCC1806, another line of human triple-negative breast cancer cells (FIG. 3D). Similar results were obtained with another assay for cancer stem cells: the mammosphere-forming capacity that is characteristic of breast cancer stem cells in cultures of MCF7 and HCC1806 cells. After co-culture for 3 days, mammosphere formation of FACS isolated breast cancer cells was increased significantly by BM-MSCs but not by iPSC-MSCs (FIG. 3E). Co-inoculation with BM-MSCs remarkably increased the tumor-initiating ability of multiple types of cancer cells including HCC1806 (Li et al., 2012). Here, we found that the tumor-initiating ability of HCC1806 cells co-inoculated with iPSC-MSCs was lower significantly than those co-inoculated with BM-MSCs when either $5 \times 10^4$ or $1 \times 10^4$ HCC1806 cancer cells were injected ($P<0.05$, FIG. 3F, data on Week 3, Week 6 data will be obtained soon).

The Activity of ILA R-PGE2-IL6 Pathway was Marginal in iPSC-MSCs

Figure 4A:
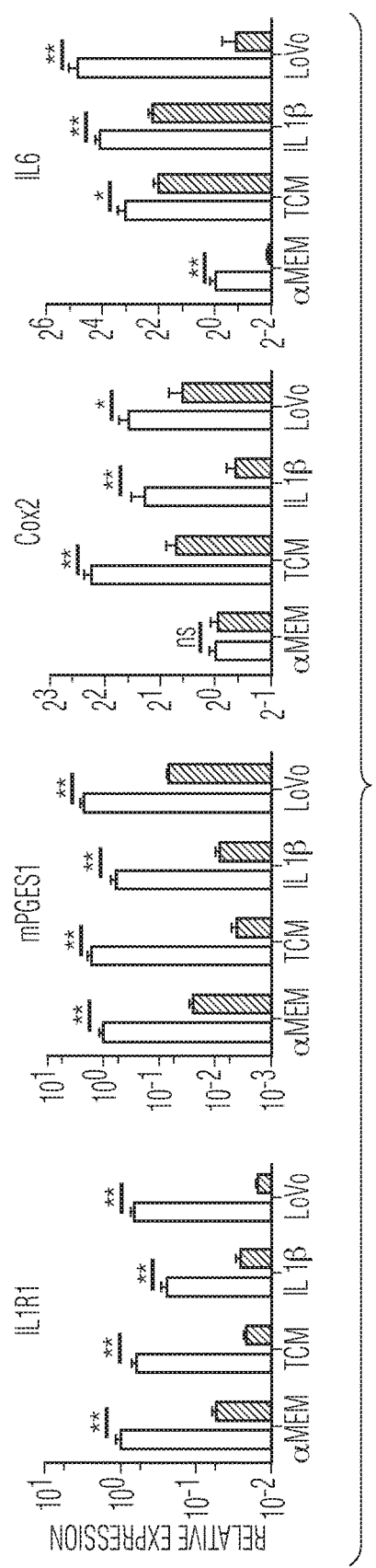
FIG. 4. The ILR-PGE2-IL6 pathway in iPSC-MSCs.
(A) qRT-PCR analysis of genes of ILR-PGE2-IL6 pathway in MSCs cultured with αMEM, Il1, LoVo conditioned medium (TCM) or cells for 3 days. (B) ELISA of PGE2 in 3-day medium of MSCs cultured under above conditions.
Figure 4B:
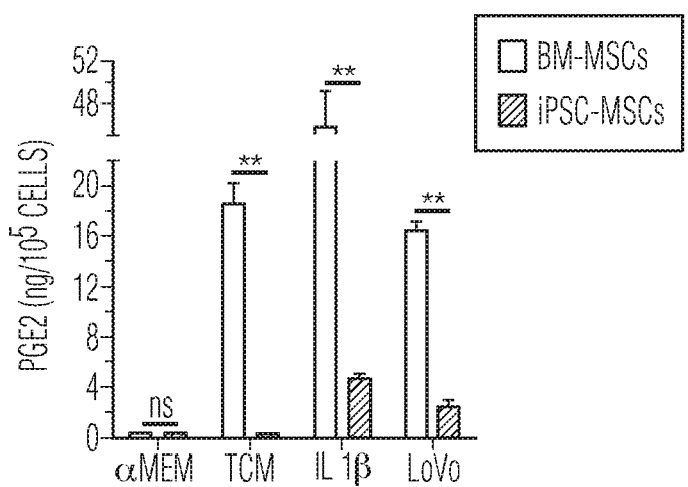

For cancer cells such as LoVo that express high level of Interleukin-1 (IL1), the pro-tumor effect of MSCs is mediated mainly by the 11 receptor (IL1R)/prostaglandin E2 (PGE2) pathway (Li et al., 2012). Our iPSC-MSCs compared to BM-MSCs expressed much lower levels of the mRNA for IL1R type 1 (IL1R1), the signal transducer of ILA pathway (Sims et al., 1993), and prostaglandin E synthase (PTGES/mPGES1). The lower levels of expression of these two genes was not affected significantly by treatment with IL1, tumor conditioned medium (TCM) from LoVo cells or co-culture with LoVo cells (FIG. 4A). The basal level of expression of cyclooxygenase-2 (Cox2/PTGS2), another key PGE2 synthase, was about the same in BM-MSCs and iPSC-MSCs cultured in αMEM, but there was less up-regulation of Cox2 in iPSC-MSCs than in BM-MSCs after treatment with IL1 or LoVo TCM or co-culture with LoVo cells (FIG. 4A, P<0.05). As expected from these observations, the level of PGE2 in the medium of iPSC-MSCs was lower than that of BM-MSCs after treatment with IL1, LoVo TCM or LoVo cells (FIG. 4B, P<0.01). As a consequence, the expression of Interleukin-6 (IL6), a major pro-tumor factor regulated by both IL1 and PGE2, was much lower in iPSC-MSCs than that in BM-MSCs under all culture conditions (FIG. 4A, P<0.05).

Figure 5A:
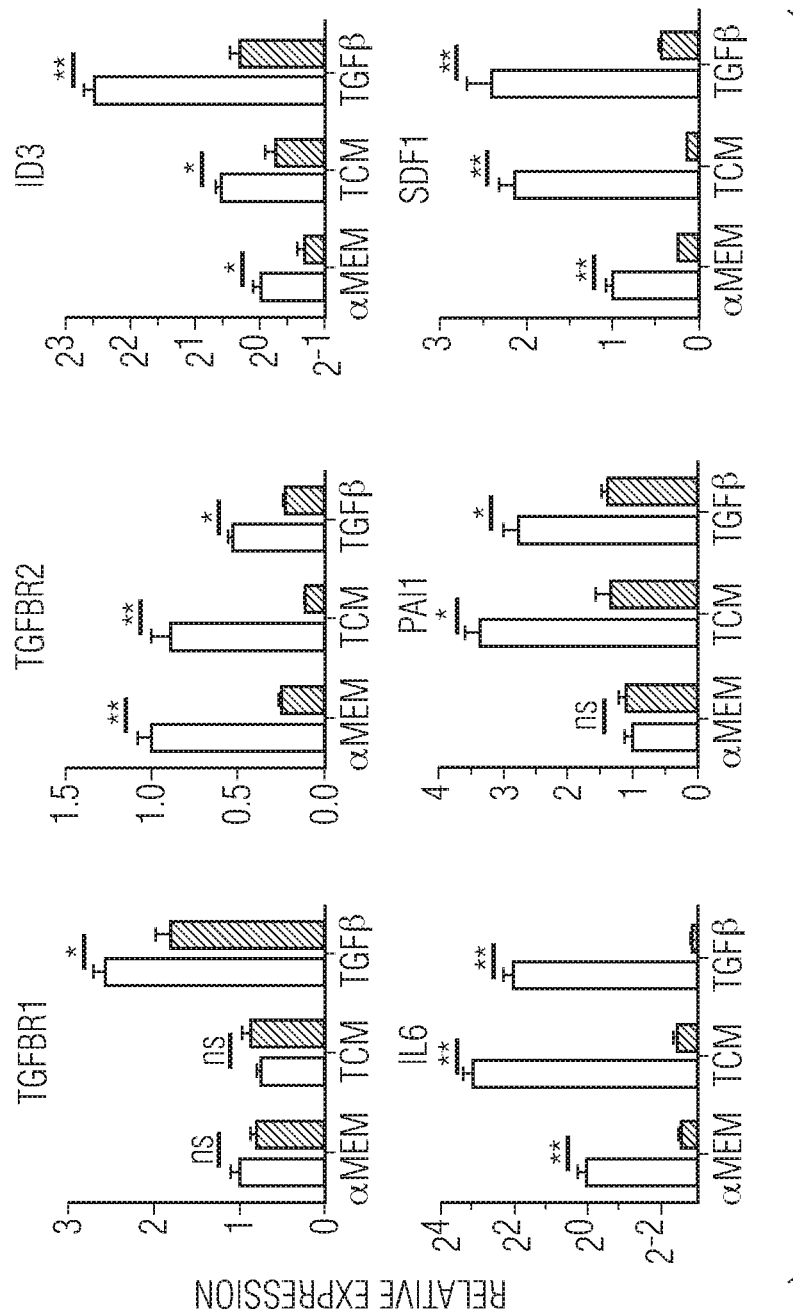
FIG. 5. The TGFβ-SDF1 pathway in iPSC-MSCs.
(A) qRT-PCR analysis of TGFβ receptors (TGFBR1 and TGFBR2), and TGFβ target genes (ID3, IL6, PAH and SDF1) in MSCs cultured with αMEM, TGFβ, or MDA-MB-231 conditioned medium (TCM) for 3 days. (B) Western blot analysis of levels of phospho-Smad2 and phospho-Smad3 in MSCs cultured in above conditions, normalized to GAPDH (n=3).
Figure 5B:
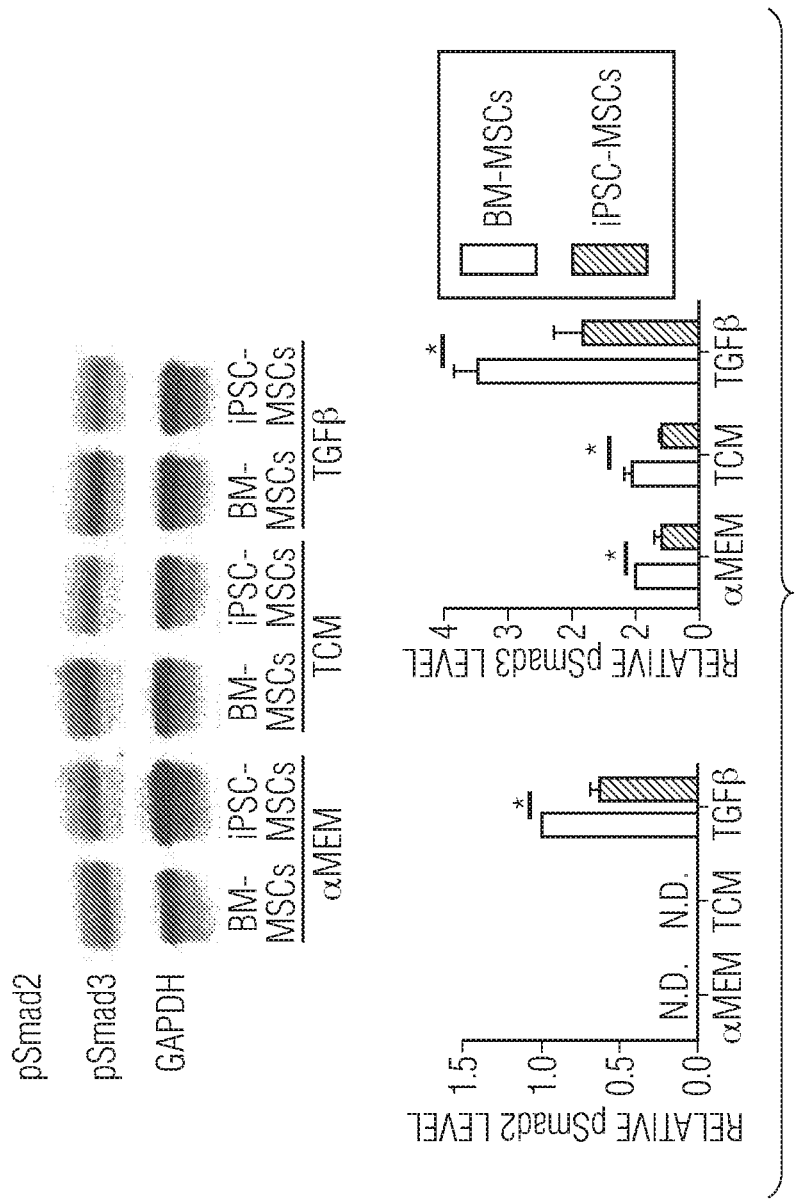
Figure 6A:
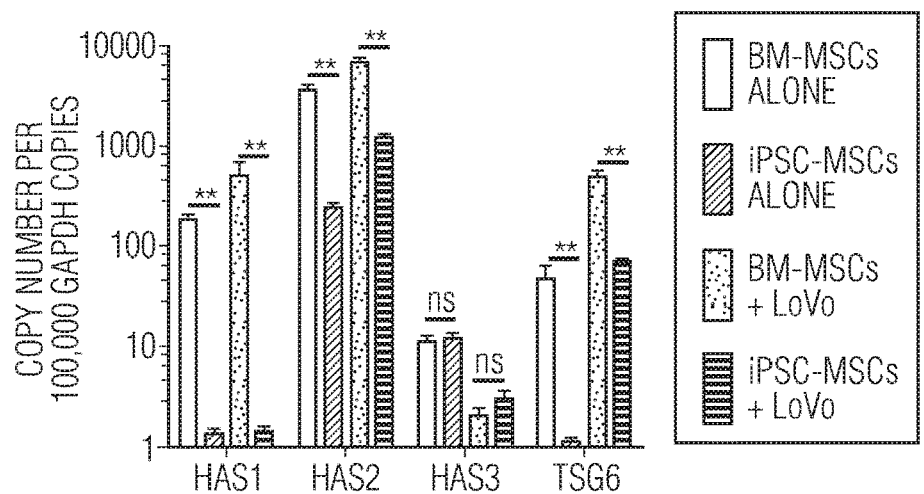
FIG. 6. The expression of HASs and TSG6 and the HA production in MSCs and the induction of LOX in cancer cells.
(A) qRT-PCR analysis of HAS1-3 and TSG6 in MSCs cultured alone or with LoVo cells for 3 days.
(B) EIA analysis of HA in 6-day medium of BM-MSCs or iPSC-MSCs at passage 5 and 15.
Figure 6B:
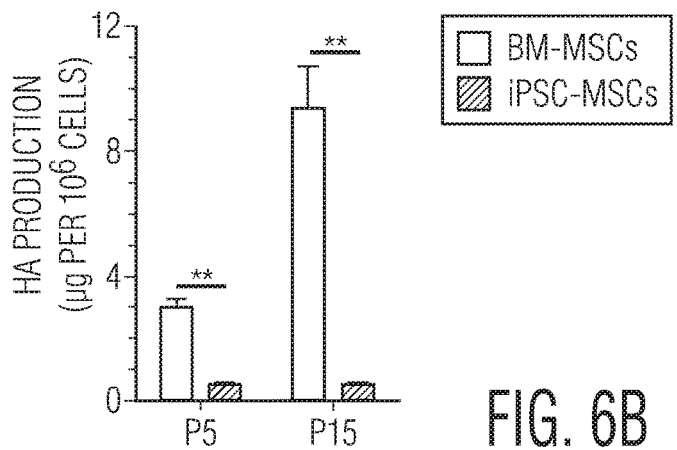
Figure 6C:
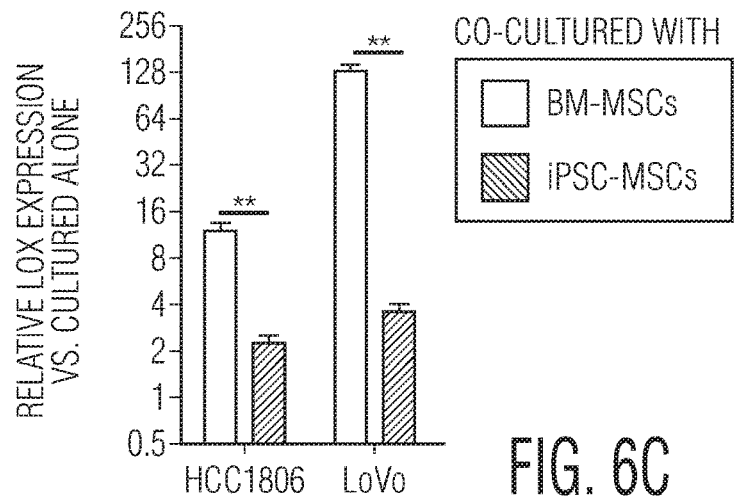

TGFβ Signaling and Production of Related Pro-Tumor Factors was Less in iPSC-MSCs than in BM-MSCs Transforming growth factor β (TGFβ) signaling is also essential for the pro-tumor effects of BM-MSCs. It increases expression of multiple pro-tumor factors such as stromal cell-derived factor 1 (SDF1/CXCL12), plasminogen activator inhibitor type 1 (PAI1/SERPINE1) and IL6 (Hogan et al., 2013; Quante et al., 2011; Shangguan et al., 2012). When cultured in αMEM, TCM from MDA-MB-231 cancer cells or treated with 10 ng/ml TGFβ1, iPSC-MSCs expressed lower levels than BM-MSCs of the TGFβ receptor type 2 (TGFβR2), and of the TGFβ target genes inhibitor of differentiation 3 (ID3) (Chambers et al., 2003), IL6 and SDF1 (P<0.05, FIG. 5A). The expression of TGFβreceptor type 1 (TGFβR1) was not different significantly between these two types of MSCs cultured in αMEM or TCM, but was lower significantly in iPSC-MSCs than that in BM-MSCs when both cells were treated with TGFβ1 (P<0.05, FIG. 5A). The expression of PAH, another TGFβ target gene (Boehm et al., 1999) with pro-tumor activities, was not different significantly between these two types of MSCs cultured in 660 MEM, but was lower significantly in iPSC-MSCs than in BM-MSCs when treated with TCM or TGFβ1 (P<0.05, FIG. 5A). Western blot analysis confirmed that the level of phospho-Smad3 was significantly lower in iPSC-MSCs than in BM-MSCs when cultured in αMEM, TCM or treated TGFβ1, whereas the level of phospho-Smad2 was undetectable in both MSCs cultured in αMEM or TCM but was lower significantly in iPSC-MSCs than that in BM-MSCs when treated with TGFβ1 (P<0.05, FIG. 5B). These data indicated that decreased TGFβ signaling also contributes to the lack of significant pro-tumor effects in iPSC-MSCs.

iPSC-MSCs Compared to BM-MSCs Produced Less Hyaluronan Acid and TSG6 and did not Upregulate Lysyl Oxidase in Co-cultured Cancer Cells One essential mechanism of the pro-tumor effects of BM-MSCs is the upregulation of lysyl oxidase (LOX) in adjacent cancer cells by triggering the CD44 signaling pathway with hyaluronan acid (HA) to promote EMT and metastasis (EI-Haibi et al., 2012). Tumor necrosis factor α-induced protein 6 (TSG6), a secreted protein highly expressed by BM-MSCs (Lee et al., 2009a), enhances or induces the binding of HA to cell surface CD44 (Lesley et al., 2004). In iPSC-MSCs, the expression of TSG6 and dominant HA synthases (NASI and HAS2) was lower dramatically than that in BM-MSCs with or without co-culture with LoVo cancer cells (FIG. 6A, P<0.01). Consistent with this observation, the amount of HA secreted into medium by iPSC-MSCs was lower significantly than by BM-MSCs at both passage 5 and 15 (FIG. 6B, P<0.01). As expected, in co-cultures with HCC1806 of LoVo cancer cells, iPSC-MSCs were less effective than BM-MSCs in upregulating the LOX mRNA in cancer cells (FIG. 6C, P<0.01). Therefore the results indicated that decreased up-regulation of LOX contributes to the lack of significant pro-EMT and pro-invasion effects of iPSC-MSCs.

Discussion

The differentiation of human iPSCs to MSCs has been reported to be much less efficient than the differentiation of embryonic stem cells (ESCs) to MSCs (20% vs. 40% $CD73^+$) (Sanchez et al., 2011). Also, the flow cytometric sorting generally is necessary to isolate iPSC-derived MSCs, a procedure that is expensive, technically challenging and may cause damage to cells. We modified the differentiation protocol initially by inhibiting Smad2/3 signaling in iPSCs cultured with chemically defined mTeSRI medium (Ludwig et al., 2006), and then passaging the cells by trypsinization (Lian et al., 2007) repeatedly (Lai et al., 2011) in 7.5% $CO_2$ (Olivier and Bouhassira, 2011), conditions that were reported previously to improve the differentiation toward MSCs. During the repeated passaging by trypsinization, we used standard tissue culture plastic dishes instead of gelatin-coated plates. The early introduction of the tissue culture plastic dishes probably accelerated selection for MSC-like cells because the dishes are pretreated under proprietary conditions to increase oxygenated derivatives on the surface of the plastic and thereby make them more hydrophilic and increase the adherence of vertebrate fibroblasts and similar cells (Ramsey et al., 1984). The selection by adherence on the treated plastic also met one of the minimal defining criteria for human MSCs (Dominici et al., 2006). This modified protocol achieved highly efficient enrichment of iPSC-MSCs (>99.6% were positive for CD73, CD105 and CD166) and eliminated the need of flow cytometric sorting. The iPSC-MSCs expanded more rapidly and to a greater extent than BM-MSCs, but still eventually underwent senescence similar to BM-MSCs. Therefore they were less likely to cause tumors or malignancies in patients than cells that are immortal in culture (Prockop and Keating, 2012). Also, the iPSC-MSCs did not form teratomas in mice.

The immunosuppressive, anti-inflammatory and differentiation properties of MSCs derived from ESCs or iPSCs have been examined by several laboratories (de Peppo et al., 2013; Sanchez et al., 2011). No analysis, however, on the tumor-homing and anti- or pro-tumor properties of ESC- or iPSC-derived MSCs has been reported. We found that our iPSC-MSCs can home to tumors with the same efficiency as BM-MSCs, but do not promote EMT, invasion, or the stemness of cancer cells as BM-MSCs do. BM-MSCs and cancer cells interact through multiple mechanisms: 1) 11 produced by cancer cells promote PGE2 production by BM-MSCs, which in turn induces expression of pro-tumor factors such as IL6 in MSCs and also promotes cancer progression directly (Li et al., 2012); 2) TGF produced by cancer cells or tumor stromal cells promotes expression of pro-tumor factors such as IL6 and SDF1 by BM-MSCs (Quante et al., 2011; Shangguan et al., 2012); 3) hyaluronan produced by MSCs activates the CD44 pathway in cancers to induce LOX expression, promote the EMT and invasion of cancer cells (El-Haibi et al., 2012). Intriguingly, the expression of multiple genes related with these three pathways, including receptors for 11 and TGFβ, IL6, SDF1, and synthases of PGE2 and hyaluronan, as well as the production of PGE2 and hyaluronan, was lower dramatically in iPSC-MSCs with or without exposure to tumor micro-environment. Together, all the factors may contribute to the significant decrease of pro-tumor potential of iPSC-MSCs. The pro-tumor effects of MSCs happen rapidly as indicated by significant upregulation of pro-EMT genes in cancer cells co-cultured with BM-MSCs for 12 hours (Li et al., 2012), suggesting that the pro-tumor risk may compromise the efficacy of anti-cancer agents delivered by MSCs and is difficult to circumvent by transducing MSCs with suicide genes.

The other advantage of iPSC-MSCs is that transgenes can be inserted into safe harbor alleles of iPS cells to eliminate the risk of insertional mutation and to guarantee the stable expression of transgenes over prolonged expansion and differentiation (Zou et al., 2011). Subsequently, MSCs can be derived from the safely engineered iPS cells. This approach is not feasible for MSCs from bone marrow or other tissues because of their limited expandability; correctly targeted clones from a single cell need to be established and then expanded extensively for therapeutic applications.

In summary, compared with BM-MSCs, iPSC-MSCs developed with our modified protocol have same tumor tropism but much less pro-tumor potential. They can also be readily genetically engineered and the protocol can be scaled up to produce large numbers of the cells. Hence, iPSC-MSCs prepared with the modified protocol provide a promising alternative to BM-MSC for therapy of cancer patients or survivors and for other applications including bioengineering.

Example 2

Sources of the TSG-6 and BMP-2 genes. To prepare a gene for TSG-6 (D-K Kim, H Choi, and D J Prockop, in prep.), we have generated a cDNA by RT-PCR of RNA from human MSCs, cloned and amplified the gene in *E. coli*, confirmed the sequence of gene, expressed the gene in CHO cells, and demonstrated that transfected CHO cells secrete TSG-6 that suppresses inflammation in the cornea model. A similar strategy is used to prepare a gene for BMP-2 from human MSCs that are differentiated into chondrocytes so that they express high levels of BMP-2 (Sekiya et al. 2002).

Insertion of the genes into "safe harbors". Three different iPSC lines are used (i) human CY2/CDI iPSCs so that the cells can be compared to iPSC-derived MSCs; (ii) a parent NCRM5 iPSC line and (iii) a reporter NCRM5 iPSC line with insertion of luciferase (NanoLuc and Halotag) in the chromosome 13 locus (NCRM5AS1-iCLHN; NIMH.SCR). A polymercleotide encoding TSG-6 or BMP-2 is inserted into the AAVS1 locus on chromosome 19. Each gene is inserted with a tetracycline inducible promoter and an rtTA gene controlled by a ubiquitous promoter obtained from Dr. Sam M. Janes (Loebinger et al., 2009). For insertions, a commercial kit (PinPoint System, System Biosciences) that employs the CRISPR technology and that has been reported to be more robust than alternate technologies such as TAL-ENS (Zhang et al., 2014) is used. Specifically, the PinPoint-HR System for Platform Cell Line Generation & Retargeting of AAVS1 Safe Harbor Locus is used (PIN412A-KIT includes PIN410A-1, CAS601A-2, PIN200A-1, PIN510A-1, & PIN600A-1). The transduced iPSCs are cloned and screened for off-target insertion. Briefly, potential off-target sites in the human genome that might be recognized by RNA-guided endonucleases specific for the AAVS1 are searched and the top-ranked sites with reported criteria (Cho et al., 2014) are chosen. Then, the frequencies of small insertions/deletions (indels) at the on-target site and putative off-target sites are measured using deep sequencing. The iPSC clones with on-target insertion but no off-target indels are used for expansion and derivation of MSCs.

Assays of the transduced cells. The transduced cells expanded from the selected iPSC clones are assayed for expression of transgenes upon doxycycline induction by qRT-PCR and ELISAs before and after differentiation to MSCs and after expansion of the iPSC-derived MSCs.

Assays for suppression of sterile inflammation in vivo. The cells transduced with TSG-6 are assayed for efficacy as described in several of our publications. (Oh et al., 2010; Roddy et al., 2011; Choi et al., 2011; Foskett et al., 2013). Dose response is evaluated in the cornea model by unbiased evaluation of opacity and MPO assays; in the peritonitis model by qRT-PCR assays for pro-inflammatory cytokines; and in the lung injury model by severe decreases in arterial oxygen saturation that threaten survival.

Assays for osteogenesis in vivo. The cells transduced to express BMP-2 are assayed in the cranial defect model that is described in several publications by our research team (Krause et al., 2010; Zeitourni et al., 2012). Efficacy is assayed by pCT and histology.

The disclosures of all patents, publications (including published patent applications), depository accession numbers, and database accession numbers are incorporated by reference to the same extent as if each patent, publication, depository accession number, and database accession number were incorporated individually by reference.

It is to be understood, however, that the scope of the present invention is not to be limited to the specific embodiments described above. The invention may be practiced

REFERENCES

Barkholt, L, Flory, E, Jekerle, Lucas-Samuel, S., Ahnert, P., Bisset, L, Buscher, D., Fibbe, W., Foussat, A., Kwa, M, et al (2013). Risk of tumorigenicity in mesenchymal stromal cell-based therapies-bridging scientific observations and regulatory viewpoints. Cytotherapy 15, 753-759.

Boehm, J. R., Kutz, S. M., Sage, E. H., Staiano-Coico, L., and Higgins, P. J. (1999). Growth state-dependent regulation of plasminogen activator inhibitor type-1 gene expression during epithelial cell stimulation by serum and transforming growth factor-betal. J Cell Physiol 181, 96-106.

Chambers, R. C., Leoni, P., Kaminski, N., Laurent, G. J., and Heller, R. A, (2003). Global expression profiling of fibroblast responses to transforming growth factor-betal reveals the induction of inhibitor of differentiation-1 and provides evidence of smooth muscle cell phenotypic switching. Am J Pathol 162, 533-546.

Chaturvedi, P., Gilkes, D. M., Wong, C. C., Kshitiz, Luo, W., Zhang, H., Wei, H., Takano, N., Schito, L., Levchenko, A., et al. (2013). Hypoxia-inducible factor-dependent breast cancer-mesenchymal stem cell bidirectional signaling promotes metastasis. J Clin Invest 123, 189-205.

Cho, S. W. Kim, S., Kim, Y., Kweon, J., Kim, H. S., Bae, S., Kim, J. S. Analysis of off-target effects of CRISPR/Cas-derived RNA-guided endonucleases and nicknases, Genome Res. 2014 January; 24(1):132-141. doi:10.1101/gr. 162339.113. Epub 2013 Nov. 19.

Choi, H., Lee, R-H, Bazkanov, N., Oh, J. Y., Prockop, D. J. Anti-inflammatory protein TSG-6 secreted by activated MSCs attenuates zymosan-induced mouse peritonitis by decreasing TLR 2/NF-kB signaling in resident macrophages. Blood 2011 July 14; 118(2):330-338. doi/10.1182/blood-2010-12-327353. Epub 2011 May 6. Pub Med PMID: 21551236; Pub Med Central PMCID:PMC 3138686.

de Peppo, G. M., Marcos-Campos, I., Kahler, D. J., Alsalman, D, Shang, L, Vunjak-Novakovic, G., and Marolt, D. (2013). Engineering bone tissue substitutes from human induced pluripotent stem cells. Proc Natl Acad Sci USA 110, 8680-8685.

Dominici, M., Le Blanc, K., Mueller, I., Slaper-Cortenbach, I., Marini, F., Krause, D, Deans, R., Keating, A., Prockop, D., and Horwitz, E. (2006). Minimal criteria for defining multipotent mesenchymal stromal cells. The International Society for Cellular Therapy position statement. Cytotherapy 8, 315-317.

Donnenberg, V. S., Zimmerlin, L, Rubin, J. P., and Donnenberg, A. D. (2010). Regenerative therapy after cancer: what are the risks? Tissue Eng Part B Rev 16, 567-575.

Droujinine, I. A., Eckert, M. A., and Zhao, W. (2013). To grab the stroma by the horns: from biology to cancer therapy with mesenchymal stem cells. Oncotarget 4, 651-664.

El-Haibi, C. P., Bell, G. W., Zhang, J., Collmann, A. Y., Wood, D., Scherber, C. M., Csizmadia, E., Mariani, O., Zhu, C., Campagne, A., et al. (2012). Critical role for lysyl oxidase in mesenchymal stem cell-driven breast cancer malignancy. Proc Natl Acad Sci USA 109, 17460-17465.

Foskett A M, Bazhanov N., Ti X, Tiblow A, Bartosh T J, Prockop D J. Phase-directed therapy: TSG-6 targeted to early inflammation improves bleomycin-injured lungs. Am J Physiol Lung Cell Mol Physiol. 2014 January; 306(2): L120-31. Doi:10.1152/ajplung.00240.2013 Nov. 15. PubMed PMID: 24242012; PubMed Central PMCID: PMC3920207.

Fritz, V., Noel, D, Bouquet, C, Opolon, P., Voide, R., Apparailly, F., Louis-Plence, P., Bouffi, C, Drissi, H., Xie, C.,et al (2008). Antitumoral activity and osteogenic potential of mesenchymal stem cells expressing the uro-kinase-type plasminogen antagonist amino-terminal fragment in a murine model of osteolytic tumor. Stem Cells 26, 2981-2990. Gregory, C. A., and Prockop, D. J. (2007). Fundamentals of Culture and Characterization of Mesenchymal Stem Cells from Bone Marrow Stroma. In Culture of Human Stem Cells, R. I. Freshney, Stacey, G. N. and Auerbach, J. M., ed. (New Jersey, USA.: Wiley-Liss).

Grisendi, G, Bussolari, R, Cafarelli, L., Petak, I., Rasini, V., Veronesi, E, De Santis, G., Spano, C, Tagliazzucchi, M., Barti-Juhasz, H., et al (2010). Adipose-derived mesenchymal stem cells as stable source of tumor necrosis factor-related apoptosis-inducing ligand delivery for cancer therapy. Cancer Res 70, 3718-3729.

Gu, J., Qian, H., Shen, L, Zhang, X., Zhu, W., Huang, L, Yan, Y, Mao, F., Zhao, C., Shi, Y. et al. Gastric cancer exosomes trigger differentiation of umbilical cord derived mesenchymal stem cells to carcinoma-associated fibroblasts through TGF-beta/Smad pathway. PLoS One 7, e52465.

Hai, B., Yang, Z., Millar, S. E., Choi, Y. S., Taketo, M. M., Nagy, A., and Liu, F. (2010). Wnt/beta-catenin signaling regulates postnatal development and regeneration of the salivary gland. Stem Cells Dev 19, 1793-1801.

Hogan, N. M., Joyce, M. R., Murphy, J. M., Barry, E P., O'Brien, T., Kerin, M. J., and Dwyer, R. M. Impact of mesenchymal stem cell secreted PAI-1 on colon cancer cell migration and proliferation. Biochem Biophys Res Commun 435, 574-579.

Ip, J. E., Wu, Y, Huang, J., Zhang, L, Pratt, R. E., and Dzau, V. J. (2007). Mesenchymal stem cells use integrin betal not CXC chemokine receptor 4 for myocardial migration and engraftment. Mol Biol Cell 18, 2873-2882.

Jung, Y, Kim, J. K., Shiozawa, Y., Wang, J., Mishra, A., Joseph, J., Berry, J. E., McGee, S., Lee, E, Sun, H, et al, (2013). Recruitment of mesenchymal stem cells into prostate tumours promotes metastasis. Nat Commun 4, 1795.

Karnoub, A. E., Dash, A. B., Vo, A. P., Sullivan, A., Brooks, M. W., Bell, G. W., Richardson, A. L., Polyak, K., Tubo, R, and Weinberg, R. A. (2007). Mesenchymal stem cells within tumour stroma promote breast cancer metastasis. Nature 449, 557-563.

Kidd, S., Spaeth, E., Watson, K., Burks, J., Lu, H., Klopp, A., Andreeff, M, and Marini, F. C. (2012). Origins of the tumor microenvironment: quantitative assessment of adipose-derived and bone marrow-derived stroma. PLoS One 7, e30563.

Klopp, A. H., Zhang, Y., Solley, T, Amaya-Manzanares, F., Marini, F., Andreeff, M., Debeb, B., Woodward, W., Schmandt, R., Broaddus, R., et al. (2012). Omental adipose tissue-derived stromal cells promote vascularization and growth of endometrial tumors. Clin Cancer Res 18,771-782, Krause U, Harris S, Green A, Ylostalo J, Zeitouni S, Lee N, Gregory C A, Pharmaceutical modulation of canonical Wnt signaling in multipotent stromal cells for improved osteoinductive therapy. Proc Natl Acad Sci USA 2010 Mar. 2; 107(9): 4147-52. doi: 10.1073/pras. 0914360107. Epub 2010 Feb. 11. PubMed PMID; 20150512; PubMed Central PMCID: PMC2840116.

Lai, R. C., Choo, A., and Lim, S. K. (2011). Derivation and characterization of human ESC-derived mesenchymal stem cells. Methods Mol Biol 698,141-150.

Larson, B. L., Ylostalo, J., Lee, R. H., Gregory, C, and Prockop, D. J. (2010). SoxII is expressed in early progenitor human multipotent stromal cells and decreases with extensive expansion of the cells. Tissue Eng Part A 16, 3385-3394.

Lee, J. H., Lee, D. S., Nam, H., Lee, G., Seo, B. M., Cho, Y. S., Bae, H. S., and Park, J. C. (2012). Dental follicle cells and cementoblasts induce apoptosis of ameloblast-lineage and Hertwig's epithelial root sheath/epithelial rests of Malassez cells through the Fas-Fas ligand pathway. Eur J Oral Sci 120, 29-37.

Lee, R. H., Pulin, A. A., Seo, M. J., Kota, D. J., Ylostalo, J., Larson, B. L, Semprun-Prieto, L., Delafontaine, P., and Prockop, D. J. (2009a). Intravenous hMSCs improve myocardial infarction in mice because cells embolized in lung are activated to secrete the anti-inflammatory protein TSG-6. Cell Stem Cell 5, 54-63.

Lee, R. H., Seo, M. J., Pulin, A. A., Gregory, C. A., Ylostalo, J., and Prockop, D. J. (2009b). The CD34-like protein PODXL and alpha6-integrin (CD49f) identify early progenitor MSCs with increased clonogenicity and migration to infarcted heart in mice. Blood 113, 816-826. Lesley, J., Gal, L, Mahoney, D. J., Cordell, M. R., Rugg, M. S., Hyman, R., Day, A. J., and Mikecz, K. (2004). TSG-6 modulates the interaction between hyaluronan and cell surface CD44. J Biol Chem 279, 25745-25754.

Li, H. J., Reinhardt, F., Herschman, H. R., and Weinberg, R. A. (2012). Cancer-Stimulated Mesenchymal Stem Cells Create a Carcinoma Stem Cell Niche via Prostaglandin E2 Signaling. Cancer Discov 2, 840-855.

Li, X., Ling, W., Pennisi, A., Wang, Y., Khan, S., Heidaran, M., Pal, A., Zhang, X., He, S, Zeitlin, A., et a/. (2011). Human placenta-derived adherent cells prevent bone loss, stimulate bone formation, and suppress growth of multiple myeloma in bone. Stem Cells 29, 263-273.

Lian, Q, Lye, E., Suan Yeo, K, Khia Way Tan, E., Salto-Tellez, M., Liu, T. M., Palanisamy, N., El Oakley, R. M., Lee, E. H., Um, B., et al. (2007). Derivation of clinically compliant MSCs from CD105+, CD24-differentiated human ESCs. Stem Cells 25, 425-436.

Lin, C. Y., Chang, F. H., Chen, C. Y., Huang, C. Y., Hu, F. C., Huang, W. K., Ju, S. S., and Chen, M. H. (2011). Cell therapy for salivary gland regeneration. J Dent Res 90, 341-346.

Liu, S., Ginestier, C, Ou, S. J., Clouthier, S. G., Patel, S. H., Monville, F, Korkaya, H., Heath, A., Dutcher, J., Kleer, C. G., etai (2011). Breast cancer stem cells are regulated by mesenchymal stem cells through cytokine networks. Cancer Res 71, 614-624.

Loebinger, M. R., Eddaoudi, A., Davies, D., and Janes, S. M. (2009). Mesenchymal stem cell delivery of TRAIL can eliminate metastatic cancer. Cancer Res 69, 4134-4142.

Ludwig, T. E., Bergendahl, V., Levenstein, M. E., Yu, J., Probasco, M. D., and Thomson, J. A. (2006). Feeder-independent culture of human embryonic stem cells. Nature methods 3, 637-646.

Meirelles Lda, S., Pontes, A. M., Covas, D. T., and Caplan, A. I. (2009). Mechanisms involved in the therapeutic properties of mesenchymal stem cells. Cytokine & growth factor reviews 20, 419-427.

Moulay, G., Boutin, S., Masurier, C, Scherman, D., and Kichler, A. (2010). Polymers for improving the in vivo transduction efficiency of AAV2 vectors. PLoS One 5, e15576.

Oh J Y, Roddy G W, Choi H, Lee R H, Ylostalo J H, Rosa R H Jr, Prockop D J. Anti-inflammatory protein TSG-6 reduces inflammatory damage to the cornea following chemical and mechanical injury. Proc Natl Acad Sci USA. 2010 Sep. 28; 107(39):16875-80, doi: 10.1073/pnas. 1012451107. Epub 2010 Sep. 13, PubMed PMID: 20837529; PubMed Central PMCID: PMC2947923.

Olivier, E. N., and Bouhassira, E. E. (2011). Differentiation of human embryonic stem cells into mesenchymal stem cells by the "raclure" method. Methods Mol Biol 690, 183-193. Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.

Prockop, D. J. (1997). Marrow stromal cells as stem cells for nonhematopoietic tissues. Science 276, 71-74.

Prockop, D. J., and Keating, A. (2012). Relearning the lessons of genomic stability of human cells during expansion in culture: implications for clinical research. Stem Cells 30, 1051-1052.

Quante, M., Tu, S. P., Tomita, H., Gonda, T, Wang, S. S., Takashi, S., Baik, G. H., Shibata, W., Diprete, B., Betz, K. S., et al. (2011). Bone marrow-derived myofibroblasts contribute to the mesenchymal stem cell niche and promote tumor growth. Cancer cell 19, 257-272.

Ramsey, W. S., Hertl, W., Nowlan, E. D., and Binkowski, N. J. (1984). Surface treatments and cell attachment. In vitro 20, 802-808.

Roddy G W, Oh J Y, Lee R H, Bartosh T J, Tlostalo J, Coble K, Rosa R H Jr, Prockop D J. Action at a distance: systemically administered adult stem/progenitor cells (MSCs) reduce inflammatory damage to the cornea without engraftment and primarily by secretion of TNF-$\alpha$ stimulated gene/protein 6. Stem Cells. 2011 October; 29(10):1572-9, doi: 10.1102/stem.708. PubMed PMID: 21837654.

Sanchez, L, Gutierrez-Aranda, I., Ligero, G., Rubio, R., Munoz-Lopez, M., Garcia-Perez, J. L., Ramos, V., Real, P. J., Bueno, C., Rodriguez, R., et al. (2011). Enrichment of human ESC-derived multipotent mesenchymal stem cells with immunosuppressive and anti-inflammatory properties capable to protect against experimental inflammatory bowel disease. Stem Cells 29, 251-262.

Sekiya, I., Vuoristo, J. T., Larson, B. L., Prockop, D. J. In vitro cartilage formation by human adult stem cells from bone marrow stroma defines the sequence of cellular and molecular events during chondrogenesis. Proc. Nat. Acad. Sci. USA 2002 Apr. 2; 99(7): 4397-4402. Epub 2002 March 26, PubMed PMID: 11917104; PubMed Central PMCID:PMC 123659.

Shangguan, L, Ti, X., Krause, U, Hai, B, Zhao, Y., Yang, Z., and Liu, F. (2012). Inhibition of TGF-beta/Smad Signaling by BAMBI Blocks Differentiation of Human Mesenchymal Stem Cells to Carcinoma-Associated Fibroblasts and Abolishes their Protumor Effects. Stem Cells 30, 2810-2819.

Sims, J. E., Gayle, M. A., Slack, J. L., Alderson, M. R., Bird, T. A., Giri, J. G., Colotta, F, Re, F., Mantovani, A., Shanebeck, K, et al. (1993). Interleukin 1 signaling occurs exclusively via the type I receptor. Proc Natl Acad Sci USA 90, 6155-6159.

Song, C., and Li, G. (2011). CXCR4 and matrix metalloproteinase-2 are involved in mesenchymal stromal cell homing and engraftment to tumors. Cytotherapy 13, 549-561. Spaeth, E. L., Labaff, A M., Toole, B. P., Klopp, A., Andreeff, M., and Marini, F. C. (2013). Mesenchymal CD44 expression contributes to the acquisition of an activated fibroblast phenotype via TWIST activation in the tumor microenvironment. Cancer Res 73, 5347-5359.

Sumita, Y., Liu, Y., Khalili, S., Maria, O. M., Xia, D., Key, S., Cotrim, A. P., Mezey, E., and Tran, S. D. (2011). Bone marrow-derived cells rescue salivary gland function in mice with head and neck irradiation. Int J Biochem Cell Biol 43, 80-87.

Viswanathan, S., Keating, A., Deans, R., Hematti, P., Prockop, D., Stroncek, D. F., Stacey, G., Weiss, D. J., Mason, C, and Rao, M. S. (2014). Soliciting Strategies for Developing Cell-Based Reference Materials to Advance MSG Research and Clinical Translation. Stem Cells Dev.

Wapnir, I. L., Barnard, N., Wartenberg, D., and Greco, R. S. (2001). The inverse relationship between microvessel counts and tumor volume in breast cancer. The breast journal 7,184188.

Yu, J., Hu, K., Smuga-Otto, K., Tian, S., Stewart, R., Slukvin, II, and Thomson, J. A. (2009). Human induced pluripotent stem cells free of vector and transgene sequences. Science 324, 797-801.

Zeitouni, S., Krause, V., Clough, B. H., Halderman, H., Falster, A., Blalock, D. T., Chaput, C. D., Sampson, H. W., Gregory, C. A. Human mesenchymal stem cell-derived matrices for enhanced osteoregeneration. Sci. Transl. Med. 2012 May 2; 4(132):132ra55.doi:10.1126/scitrans/med.3003396. Erratum in:Sci. Transl. Med. 2012 Aug. 9; 4(149):149er5. PubMed PMID:22553253.

Zhang, F., Wen, Y., Guo, X. CRISPR/Cas 9 for genome editing: progress, implications, and challenges. Hum. Mol. Genet. 2014 Apr. 7. [Epub ahead of print] PubMed PM1D:24651067.

Zimmerlin, L., Park, T. S., Zambidis, E. T., Donnenberg, V. S., and Donnenberg, A. D. (2013). Mesenchymal stem cell secretome and regenerative therapy after cancer. Biochimie 95, 2235-2245.

Zou, J., Sweeney, C. L., Chou, B. K., Choi, U., Pan, J., Wang, H., Dowey, S. N., Cheng, L, and Malech, H. L. (2011). Oxidase-deficient neutrophils from X-linked chronic granulomatous disease iPS cells: functional correction by zinc finger nuclease-mediated safe harbor targeting. Blood 117, 5561-5572.

What is claimed is:

1. A population of isolated mesenchymal stem cells produced from human induced pluripotent stem cells (iPSC-MSCs) that express no more than 1% of the levels of the Nanog, octamer-binding transcription factor 4 (Oct 4), epithelial-type cadherin (Ecad), and forkhead box A2 (Foxa 2) genes than the induced human pluripotent stem cells (iPSCs) from which said human iPSC-MSCs cells were produced, and wherein said isolated human iPSC-MSCs express lower levels of mRNA encoding IL-1 R type 1 (IL1R1), prostaglandin E synthase (PTGS2), and Interleukin -6 (IL6) than human mesenchymal stem cells obtained from bone marrow (BM-MSCs) cultured under the same condition as iPSC-MSCs and produce lower levels of PGE2 in culture medium after treatment with IL1 than human BM-MSCs, said isolated human iPSC-MSCs produced by a method comprising:
   a. culturing said iPSCs in a medium containing a TGF-β inhibitor and in an atmosphere containing from about 7 vol. % to about 8 vol. % CO2 for a period of time from about 20 days to about 35 days;
   b. transferring said cells from step (a) to a culture dish having a hydrophilic surface and culturing said cells in a medium containing a TGF-β inhibitor for a period of time sufficient to produce human mesenchymal stem cells that express no more than 1% of the levels of the Nanog, Oct 4, Ecad, and Foxa 2 genes than the iPSCs from which said human mesenchymal stem cells were produced; and
   c. isolating said human mesenchymal stem cells produced in step (b) from said medium, thereby obtaining said isolated human iPSC-MSCs that express no more than 1% of the levels of the Nanog, Oct 4, Ecad, and Foxa 2 genes than the iPSCs from which said human mesenchymal stem cells were produced, and express lower levels of mRNA encoding IL1R1, PTGS2 and IL6 than human BM-MSCs cultured under the same condition as iPSC-MSCs and produce lower levels of PGE2 in culture medium after treatment with IL1 than human BM-MSCs.

2. The isolated human mesenchymal stem cells of claim 1 wherein said isolated human mesenchymal stem cells are at least 95% positive for CD73, CD105, and CD166.

3. The isolated human mesenchymal stem cells of claim 1 where said isolated human mesenchymal stem cells are at least 85% positive for CD44 and CD90.

4. The isolated human mesenchymal stem cells of claim 1 wherein said isolated human mesenchymal stem cells are no more than 5% positive for HLA-DR, CD11b, CD24, CD34, and CD45.

5. The isolated human mesenchymal stem cells of claim 1 wherein said isolated human mesenchymal stem cells have been genetically engineered with at least one polynucleotide encoding a biologically active protein or polypeptide or a biologically active fragment, derivative, or analogue thereof.

6. The isolated human mesenchymal stem cells of claim 5 wherein said at least one biologically active protein or polypeptide or biologically active fragment, derivative, or analogue thereof is an anti-inflammatory agent or inflammation modulatory agent or a biologically active fragment, derivative, or analogue thereof.

7. The isolated human mesenchymal stem cells of claim 5 wherein said at least one biologically active protein or polypeptide or biologically active fragment, derivative, or analogue thereof is an anti-tumor agent.

8. The isolated human mesenchymal stem cells of claim 5 wherein said at least one biologically active protein or polypeptide or a biologically active fragment, derivative, or analogue thereof is tumor necrosis factor alpha stimulating gene 6 (TSG-6) protein or a biologically active fragment, derivative, or analogue thereof.

9. The isolated human mesenchymal stem cells of claim 5 wherein said at least one biologically active protein or polypeptide or biologically active fragment, derivative, or analogue thereof is a negative selective marker.

10. The isolated human mesenchymal stem cells of claim 9 wherein said negative selective marker is caspase 9.

11. The isolated human mesenchymal stem cell of claim 9 wherein said negative selective marker is Herpes Simplex Virus thymidne kinase.

12. The isolated human mesenchymal stem cells of claim 9 wherein said polynucleotide encoding a negative selective marker is under the control of an inducible promoter.

* * * * *